US008841329B2

(12) United States Patent
Shi et al.

(10) Patent No.: US 8,841,329 B2
(45) Date of Patent: Sep. 23, 2014

(54) NICOTINIC ATTENUATION OF CNS INFLAMMATION AND AUTOIMMUNITY

(75) Inventors: Fu-Dong Shi, Scottsdale, AZ (US); Ronald J. Lukas, Phoenix, AZ (US); Timothy Vollmer, Parker, CO (US)

(73) Assignee: Dignity Health, Phoenix, AZ (US)

( * ) Notice: Subject to any disclaimer, the term of this patent is extended or adjusted under 35 U.S.C. 154(b) by 190 days.

(21) Appl. No.: 13/063,713

(22) PCT Filed: Sep. 11, 2009

(86) PCT No.: PCT/US2009/056671
§ 371 (c)(1),
(2), (4) Date: May 5, 2011

(87) PCT Pub. No.: WO2010/030887
PCT Pub. Date: Mar. 18, 2010

(65) Prior Publication Data
US 2012/0322832 A1 Dec. 20, 2012

Related U.S. Application Data

(60) Provisional application No. 61/096,170, filed on Sep. 11, 2008.

(51) Int. Cl.
*A61K 31/44* (2006.01)
*A61K 31/00* (2006.01)
*A61K 31/685* (2006.01)
*A61K 31/465* (2006.01)
*A61K 45/06* (2006.01)
*A61K 31/70* (2006.01)

(52) U.S. Cl.
CPC .............. *A61K 31/00* (2013.01); *A61K 31/685* (2013.01); *A61K 31/465* (2013.01); *A61K 45/06* (2013.01); *A61K 31/70* (2013.01)
USPC ...................................... 514/343

(58) Field of Classification Search
USPC ................................. 514/334, 343
See application file for complete search history.

(56) References Cited

U.S. PATENT DOCUMENTS

| | | | |
|---|---|---|---|
| 5,470,852 A | 11/1995 | Peng et al. | |
| 2004/0167172 A1 | 8/2004 | Gwynne et al. | |
| 2006/0142180 A1* | 6/2006 | Shytle et al. | 514/2 |
| 2007/0060588 A1 | 3/2007 | Ji et al. | |
| 2008/0051444 A1 | 2/2008 | Pieper et al. | |
| 2008/0275028 A1 | 11/2008 | Gaviraghi et al. | |
| 2009/0196912 A1* | 8/2009 | Eickhoff et al. | 424/450 |
| 2009/0209480 A1* | 8/2009 | Abrams et al. | 514/46 |
| 2010/0130474 A1 | 5/2010 | Bothmann et al. | |
| 2011/0312894 A1 | 12/2011 | Wu | |
| 2013/0045987 A1 | 2/2013 | Wu | |
| 2013/0231290 A1 | 9/2013 | Wu | |

FOREIGN PATENT DOCUMENTS

| | | |
|---|---|---|
| WO | 2004108668 A3 | 12/2004 |
| WO | 2008112278 A3 | 9/2008 |
| WO | 2010030887 A1 | 3/2010 |
| WO | 2010083445 A1 | 7/2010 |
| WO | 2010088400 A1 | 8/2010 |
| WO | 2011139983 A1 | 11/2011 |
| WO | 2012068553 A3 | 5/2012 |

OTHER PUBLICATIONS

Shi et al., Nicotinic attentuation of central nervous system inflammation and autoimmunity. The Journal of Immunology, 2009, 182:1730-1739.
Alkondon et al., A single in vivo application of cholinesterase inhibitors has neuron type-specific effects on nicotinic receptor activity in guinea pig hippocampus. The Journal of Pharmacology and Experimental Therapeutics, 2009, 328 (1):69-82.
Aracava et al., Memantine blocks α7* nicotinic acetylcholine receptors more potently than n-methyl-d-aspartate receptors in rat hippocampal neurons, The Journal of Pharmacology and Experimental Therapeutics, 2005, 312 (3):1195-1205.
Hilmas et al., The brain metabolite kynurenic acid inhibits α7 nicotinic receptor activity and increases non-α7 nicotinic receptor expression: physiopathological implications, The Journal of Neuroscience, 2001 21(19):7463-7473.
Dziewczapolski et al., Deletion of the α7 nicotinic acetylcholine receptor gene improves cognitive deficits and synaptic pathology in a mouse model of alzheimer's disease, The Journal of Neuroscience, 2009, 29(27):8805-8815.
Armishaw et al., A synthetic combinatorial strategy for developing α-conotoxin analogs as potent α7 nicotinic acetylcholine receptors antagonists, The Journal of Biological Chemistry, 2010, 285(3):1809-1821.
Armishaw et al., Rational design of α-conotoxin analogues targeting α7 nicotinic acetylcholine receptors, The Journal of Biological Chemistry, 2009, 284(14):9498-9512.
Chin et al., Amyloid β protein modulates glutamate-mediated neurotransmission in the rat basal forebrain: involvement of presynaptic neuronal nicotinic acetylcholine and metabotropic glutamate receptors, The Journal of Neuroscience, 2007, 27(35): 9262-9269.
Huang et al. Modeling Differential Binding of α4β2 Nicotinic Acetylcholine Receptor with Agonists and Antagonists. J. Am. Chem. Soc. (2008). 130:16691-16696 (Abstract Only).
PCT/US2011/061541 Notification of transmittal of the international search report and written opinion dated May 25, 2012, 10 pages.
PCT/US2011/061541 International Preliminary Report on Patentability dated May 21, 2013, 6 pages.
PCT/US2010/022424 International Search Report dated Sep. 6, 2010, 4 pages.

(Continued)

Primary Examiner — My-Chau T Tran
(74) Attorney, Agent, or Firm — Sean D. Senn; Nixon Peabody LLP

(57) ABSTRACT

The present invention relates to methods of treating and/or ameliorating the severity of inflammation and autoimmunity in the central nervous system (CNS). In one embodiment, the present invention provides a method of treating multiple sclerosis by administering a therapeutically effective dosage of nicotine, or a pharmaceutical equivalent, analog, derivative, or salt thereof.

12 Claims, 19 Drawing Sheets

(56) References Cited

OTHER PUBLICATIONS

PCT/US2010/022424 Written Opinion dated Jun. 9, 2010, 5 pages.
PCT/US2010/022424 International Preliminary Report on Patentability dated Aug. 2, 2011, 6 pages.
PCT/US2009/056671 Written Opinion dated Jan. 20, 2010, 6 pages.
PCT/US2009/056671 International Preliminary Report on Patentability dated Mar. 15, 2011, 7 pages.
PCT/US2010/021250 International Search Report dated May 20, 2010, 4 pages.
PCT/US2010/021250 Written Opinion dated May 20, 2010, 6 pages.
PCT/US2010/021250 International Preliminary Report on Patentability dated Jul. 19, 2011, 7 pages.
PCT/US2011/034834 International Search Report dated Jul. 15, 2011, 2 pages.
PCT/US2011/034834 Written Opinion dated Jul. 15, 2011, 5 pages.
PCT/US2011/034834 International preliminary report on patentability dated Nov. 6, 2012, 6 pages.
Lin et al. Regulation of ATP-sensitive potassium channel function by protein kinase A-mediated phosphorylation in transfected HEK293 cells. European Molecular Biology Organization. (2000). 19(5):942-955.
Liu et al. A Novel Nicotinic Acetylcholine Receptor Subtype in Basal Forebrain Cholinergic Neurons with High Sensitivity to Amyloid Peptides. J Neuroscience. (2009). 29(4):918-929.
Palop et al. Synaptic Depression and Aberrant Excitatory Network Activity in Alzheimer's Disease: Two Faces of the Same Coin. Neuromolecular Med. (2010). 12(1):48-55.
Ferger et al. Effects of cytisine on hydroxy radicals in vitro and MPTP-induced dopamine depletion in vivo. Eur J Pharmacol. (1998). 360(2-3):155-63. Abstract Only.
Spivak et al. The Endocannabinoid Anandamide Inhibits the Function of a4B2 Nicotinic Acetylcholine Receptors. Mol. Pharmacol (2007). 72(4): 1024-1032.
Sun et al. Oral bioavailability and brain penetration of (−)-stepholidine, a tetrahydroprotoberberine agonist at dopamine D1 and antagonist at D2 receptors, in rats. British Journal of Pharmacology (2009). 158:1302-1312.
Radad et al. Short review on dopamine agonists: insight into clinical and research studies relevant to Parkinson's disease. Pharmacological Reports. (2005). 57:701-712.
Uki et al. Suppression of the Nicotinic Acetylcholine Response in Rat Superior Cervical Ganglionic Neurons by Steroids. J. Neurochem. (1999). 72(2):808-14. Abstract Only.
U.S. Appl. No. 13/146,625 Restriction Requirement dated Sep. 5, 2012, 7 pages.
U.S. Appl. No. 13/146,625 Non-Final Office Action dated Nov. 28, 2012, 19 pages.
U.S. Appl. No. 13/146,625 Final Office Action dated Apr. 4, 2013, 15 pages.
U.S. Appl. No. 13/885,534 Restriction Requirement dated Aug. 6, 2013, 10 pages.
U.S. Appl. No. 13/695,407 Restriction Requirement dated Aug. 30, 2013, 9 pages.
Wu, J. et al. 1997, Tetrahydroberberine inhibits acetylcholine-induced K+ current in acutely dissociated rat hippocampal CA1 pyramidal neurons, 1997, Elsevier, Neuroscience Letters 222, pp. 115-118.
Zwilling et al., Kynurenine 3-Monooxygenase Inhibition in Blood Ameliorates Neurodegeneration, Cell 145, 863-874, Jun. 10, 2011.
Reinhart et al., Treating the Periphery to Ameliorate Neurodegenerative Diseases, Cell 145, Jun. 10, 2011.
A Randomized Clinical Trial of Vitamin E and Memantine in Alzheimer's Disease, clinicaltrials.gov/ct2/show/record/NCT00235716?term=TEAM-AD&rank=1, 5 pages, Dec. 11, 2013.
A New Hope Oral Slow-Release Compound Protects Mice From Neurodegenerative Damage, http://www.cell.com/fulltext/S0092-8674(11)00581-2, 3 pages, Dec. 11, 2013.
Murray et al., α7β2 nAChRs assemble and function, and are activated primarily via their α7-α7 interfaces, Molecular Pharmacology Fast Forward. Published on Oct. 28, 2011 as doi:10.1124/mol.111.074088; MOL #74088.
Mowrey et al., Insights into Distinct Modulation of α7 and α7β2 nAChRs by the Volatile Anesthetic Isoflurane, J. Biol. Chem. published online Nov. 5, 2013, 19 pages.
Liu et al., Functional alpha7beta2 nicotinic acetylcholine receptors expressed in hippocampal interneurons exhibit high sensitivity to pathological level of amyloid beta peptides, BMC Neuroscience 2012, 13:155, 24 pages.

* cited by examiner

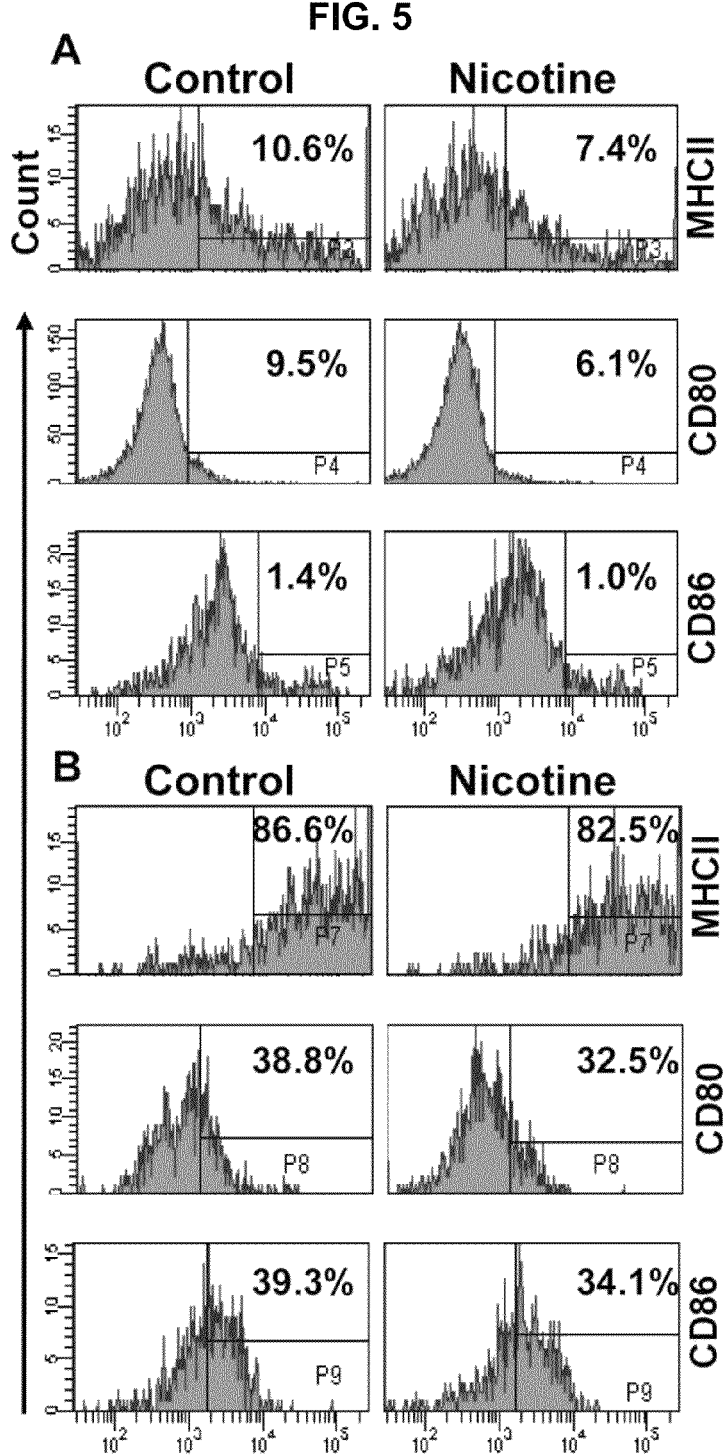

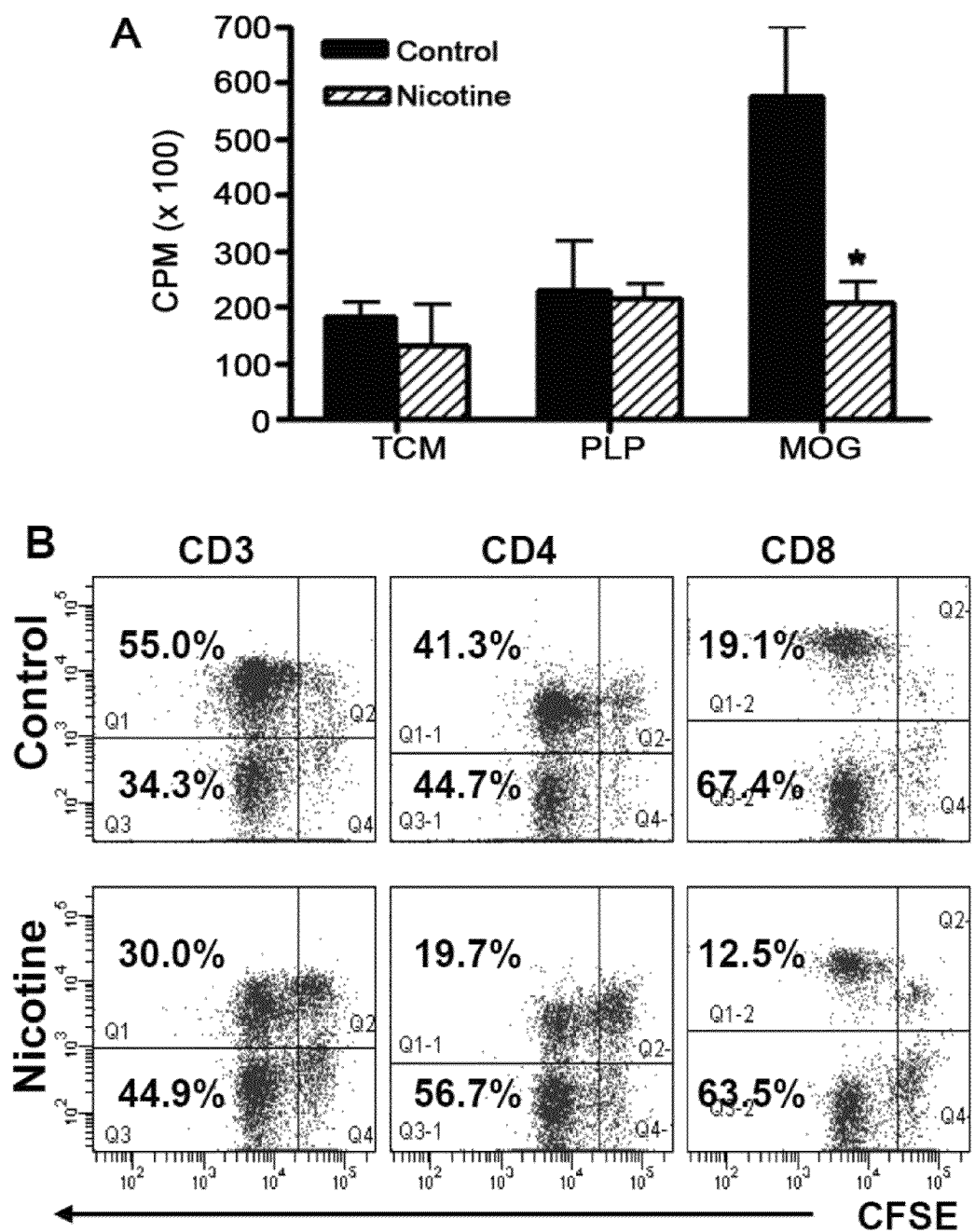

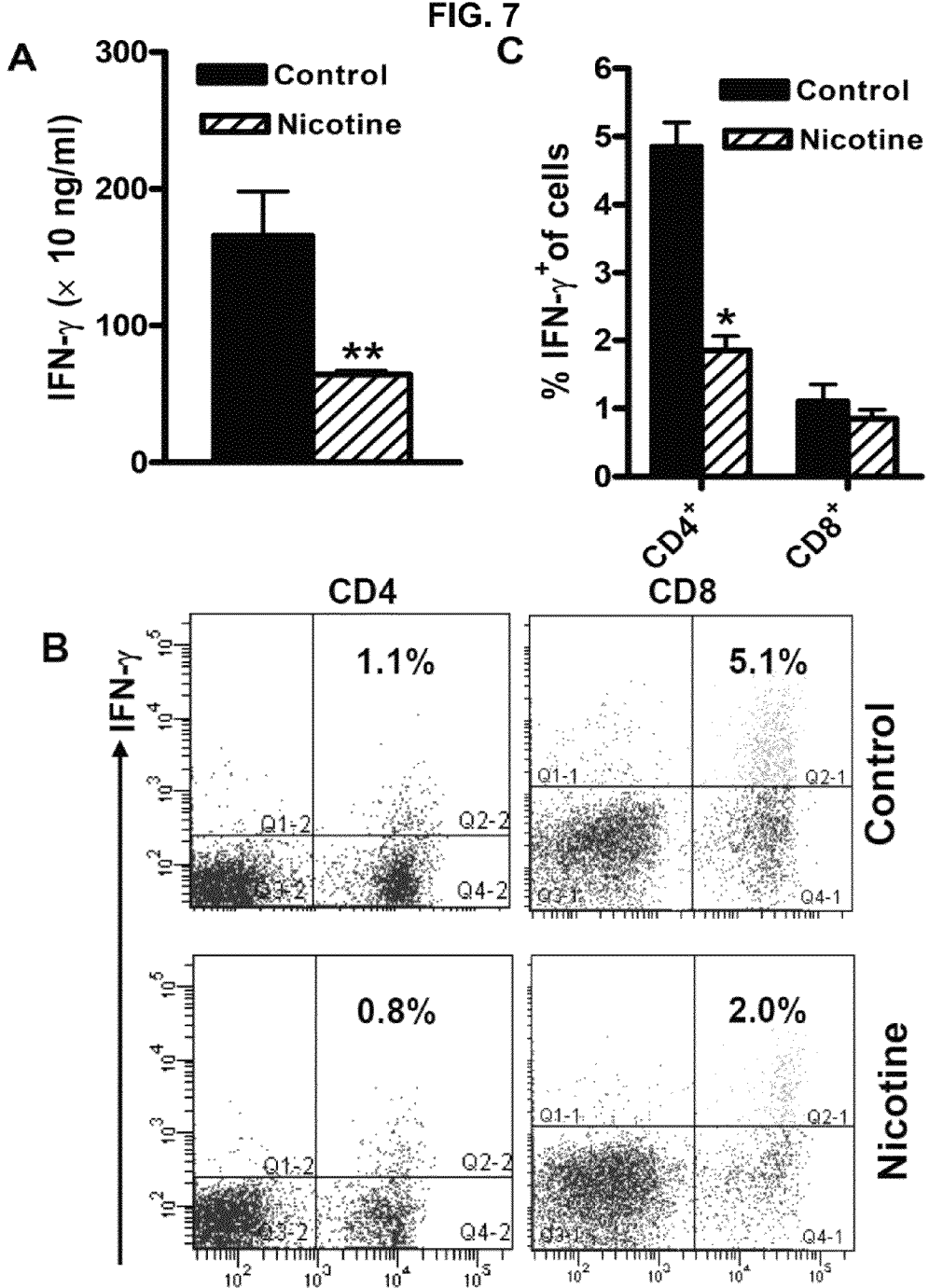

SEQUENCE LISTING

<160> NUMBER OF SEQ ID NOS: 2

<210> SEQ ID NO 1
<211> LENGTH: 22
<212> TYPE: PRT
<213> ORGANISM: Homo sapiens

<400> SEQUENCE: 1

Met Glu Val Gly Trp Tyr Arg Ser Pro Phe Ser Arg Val Val His Leu
1               5                   10                  15

Tyr Arg Asn Gly Lys Glu
            20

<210> SEQ ID NO 2
<211> LENGTH: 13
<212> TYPE: PRT
<213> ORGANISM: Homo sapiens

<400> SEQUENCE: 2

His Ser Leu Gly Lys Trp Leu Gly His Pro Asp Lys Phe
1               5                   10

NICOTINIC ATTENUATION OF CNS INFLAMMATION AND AUTOIMMUNITY

CROSS-REFERENCE TO RELATED APPLICATIONS

This application is the National Phase of International Application PCT/US09/56671, filed Sep. 11, 2009, which designated the U.S. and that International Application was published under PCT Article 21(2) in English. This application also includes a claim of priority under 35 U.S.C. §119(e) to U.S. provisional patent application No. 61/096,170, filed Sep. 11, 2008.

GOVERNMENT RIGHTS

This invention was made with U.S. Government support on behalf of the National Institute of Health by NIH Grant R01 AI052463. The U.S. Government may have certain rights in this invention.

BACKGROUND

All publications herein are incorporated by reference to the same extent as if each individual publication or patent application was specifically and individually indicated to be incorporated by reference. The following description includes information that may be useful in understanding the present invention. It is not an admission that any of the information provided herein is prior art or relevant to the presently claimed invention, or that any publication specifically or implicitly referenced is prior art.

Previous studies have suggested that nicotine, an endogenous neurotransmitter and psychoactive component of cigarette smoking, has profound immunological effects (McAlister-Sistilli, C. G., et al., *Psychoneuroendocrinology* 23:175-187; Sopori, M., *Nat Rev Immunol* 2:372-377). During ontogeny, nicotine elevates expression of the recombinase-activating gene on developing thymocytes in the thymus (Middlebrook, A. J., et al., *Immunol* 169:2915-2924) and regulates B cell development in the bone marrow (Skok, M. V., et al., *Life Sci* 80:2334-2336). For mature lymphocytes, nicotine suppresses the T cell response and alters the differentiation, phenotype and functions of antigen-presenting cells (APCs) including dendritic cells (Nouri-Shirazi, M., et al., *Immunol Lett* 109:155-164; Guinet. E., et al., *Immunol Lett* 95:45-55) and macrophages (Floto, R. A., et al., *Lancet* 361:1069-1070).

The impact of nicotine on immune responses in vivo, however, is extremely complex depending on the dosage, the duration of exposure as well as the involvement of specific organ systems in which immune responses evolve. Nicotine dampens inflammation and reduces mortality in a mouse model of sepsis (Wang, H., H. et al., *Nat Med* 10:1216-1221). This compound additionally reduces the incidence of type I diabetes in mice (Mabley, J. G., et al., *J Pharmacol Exp Ther* 300:876-881) and alters humoral autoimmunity in the experimental model, systemic lupus erythematosus (SLE) of mice (Rubin, R. L. et al., *Toxicol Sci* 87:86-96). Several epidemiological studies reveal a strong inverse correlation between smoking and the autoimmune response, the clinical manifestations of SLE and ulcerative colitis (Rubin, R. L. et al., *Toxicol Sci* 87:86-96; Jani, N., et al., *Gastroenterol Clin North Am* 31:147-166). Other studies suggest that smoking might be associated with the exacerbation of multiple sclerosis (MS) and Crohn's disease (Emre, M., et al., *Arch Neurol* 49:1243-124; Friend, K. B., et al., *Disabil Rehabil* 28:1135-1141; Johnson, G. J., et al., *Aliment Pharmacol Ther* 21:921-931). Confounding factors conferring disease exacerbation, as well as dosage and duration of smoking in these studies likely contribute to the discrepancy observed between the possible positive vs. negative effects of nicotine.

Inflammatory and immune responses within the central nervous system (CNS) are capable of shaping the clinical outcome of CNS diseases including stroke, trauma, Alzheimer's disease, Parkinson's disease, epilepsy, encephalomyelitis and MS (Zipp, F., et al., *Trends Neurosci* 29:518-527). Compared to other organ systems, the CNS has several unique properties with respect to immune responses. First, the spectrum of APCs differs from that in the periphery, because in the CNS, resident microglia and astrocytes are active participants (Ponomarev, E. D., et al., *J Immunol* 178:39-48; Simard, A. R., et al., *Mol Psychiatry* 11:327-335). Second, cells from the periphery that migrate into the CNS encounter myelin and other antigens, then undergo reactivation enhancing their capacity to recognize a wide spectrum of ambient antigens, a process defined as determinant spreading (McMahon, E. J., et al., *Nat Med* 11:335-339). Third, given the physical proximity of neuronal cells, the nature and magnitude of immune responses within the CNS are likely influenced by signals stemming directly from the local environment. Despite the quite extensive literature on the impact of nicotine on immune responses in various organ systems, the influence of nicotine on CNS inflammation has not been investigated.

Accordingly, there is a need in the art for greater understanding of the role of nicotine in CNS inflammation, as well as a need to develop novel methods of treatment for conditions associated with CNS inflammation and autoimmunity.

SUMMARY OF THE INVENTION

Various embodiments include a method of treating a disease or condition in a subject, comprising providing a composition comprising a nicotinic receptor agent, and administering a therapeutically effective dosage of the composition to the subject. In another embodiment, the nicotinic receptor is an $\alpha 7$ nicotinic acetylcholine receptor. In another embodiment, the subject is a mouse. In another embodiment, the therapeutically effective dosage of the nicotinic receptor agent ranges from 1 mg nicotine free base/kg to 60 mg nicotine free base/kg. In another embodiment, the therapeutically effective dosage of the nicotinic receptor agent is about 13 mg nicotine free base/kg/day administered over a period of 7 days. In another embodiment, the subject is a human. In another embodiment, the therapeutically effective dosage of the nicotinic receptor agent ranges from nicotine plasma levels of 1 ng/mL to 100 ng/mL. In another embodiment, the therapeutically effective dosage of the nicotinic receptor agent is a nicotine plasma level of about 30 ng/mL. In another embodiment, the therapeutically effective dosage of the nicotinic receptor agent ranges from 0.1 mg to 5 mg. Other embodiments include the therapeutically effective dosage of the nicotinic receptor agent as about 1 mg. In other embodiments, the therapeutically effective dosage of the nicotinic receptor agent ranges from 0.015 mg/kg/day to 0.6 mg/kg/day administered over a period of 7 days. In another embodiment, the disease or condition is multiple sclerosis (MS). In another embodiment, the disease or condition is acute disseminated encephalomyelitis. In another embodiment, the disease or condition is experimental autoimmune encephalomyelitis (EAE). In another embodiment, the disease or condition is a neuroimmunological disease. In another embodiment, the nicotinic receptor agent is administered to the subject continuously by an implanted pump. In another embodiment, the nicotinic receptor agent is administered by direct injection to the subject. In another embodiment, the nicotinic receptor agent comprises nicotine, or a pharmaceutical equivalent, analog, derivative, or salt thereof. In another embodiment, the nicotinic receptor agent comprises one or more substances listed in Table 1. In another embodiment, the nicotinic receptor agent comprises nicotine bitartrate.

Other embodiments include a method of treating a disease in a subject, comprising providing a composition comprising a nicotinic receptor agent, and administering a therapeutically effective dosage of the composition to enhance the activity of a compound that treats the disease. In another embodiment, the disease is MS. In another embodiment, the disease is a neuroimmunological disease.

Other embodiments include a method for the treatment of a disease and an associated condition, comprising administering a first composition in an amount effective to treat the disease, administering a therapeutically effective dosage of a second composition comprising a nicotinic receptor agent to treat the associated condition. In another embodiment, the disease is MS. In another embodiment, the disease is a neuroimmunological disease. In another embodiment, the associated condition is inflammation. In another embodiment, the associated condition is an autoimmune effect.

Other features and advantages of the invention will become apparent from the following detailed description, taken in conjunction with the accompanying drawings, which illustrate, by way of example, various embodiments of the invention.

BRIEF DESCRIPTION OF THE FIGURES

Exemplary embodiments are illustrated in referenced figures. It is intended that the embodiments and figures disclosed herein are to be considered illustrative rather than restrictive.

DESCRIPTION OF THE INVENTION

All references cited herein are incorporated by reference in their entirety as though fully set forth. Unless defined otherwise, technical and scientific terms used herein have the same meaning as commonly understood by one of ordinary skill in the art to which this invention belongs. Singleton et al., *Dictionary of Microbiology and Molecular Biology* 3$^{rd}$ ed., J. Wiley & Sons (New York, N.Y. 2001); March, *Advanced Organic Chemistry Reactions, Mechanisms and Structure* 5$^{th}$ ed, J. Wiley & Sons (New York, N.Y. 2001); and Sambrook and Russel, *Molecular Cloning: A Laboratory Manual* 3rd ed., Cold Spring Harbor Laboratory Press (Cold Spring Harbor, N.Y. 2001), provide one skilled in the art with a general guide to many of the terms used in the present application.

One skilled in the art will recognize many methods and materials similar or equivalent to those described herein, which could be used in the practice of the present invention. Indeed, the present invention is in no way limited to the methods and materials described.

As used herein, "EAE" means experimental autoimmune encephalomyelitis.

As used herein, "CNS" means central nervous system.

As used herein, "MS" means multiple sclerosis.

As used herein, "PBS" means phosphate-buffered saline.

Figure 11:
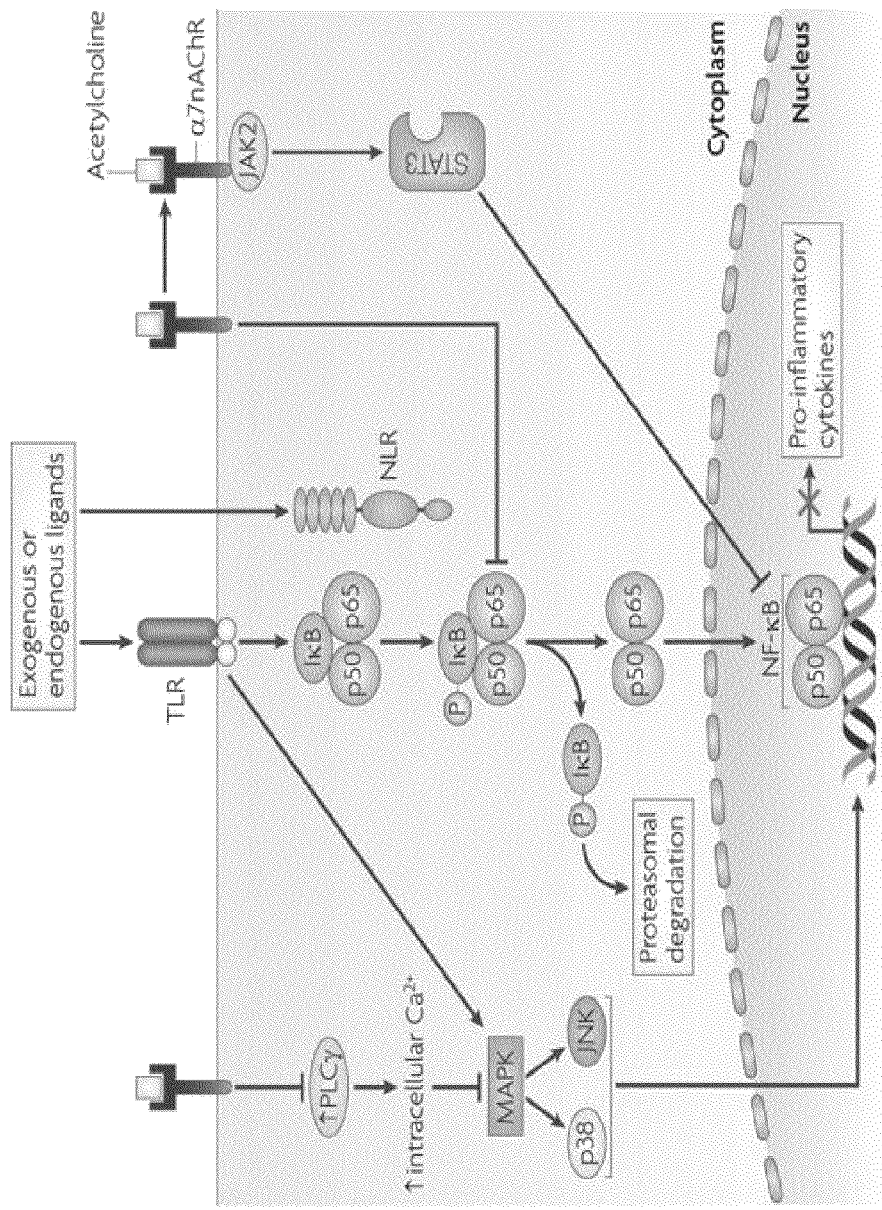
FIG. 11 (prior art) depicts an example of a signaling pathway of the α7 nAChR. In the cholinergic anti-inflammatory pathway, acetylcholine binding to nicotinic acetylcholine receptor subunit α7 (α7nAChR) leads to the inhibition of the phosphorylation of inhibitor of NF-κB (IκB), the downregulation of the activation of mitogen-activated protein kinases (MAPKs), inhibition of the release of intracellular Ca$^{2+}$ stores and the formation of a heterodimeric protein complex with Janus kinase 1 (JAK2), which activates signal transducer and activator of transcription 2 (STAT3). Together, these signaling cascades lead to inhibition of pro-inflammatory cytokine release.

As used herein, "nicotinic receptor agent" means a compound(s) and/or composition that may function similarly to, or have a similar effect as nicotine, including such compound(s) that includes nicotine, or a pharmaceutical equivalent, analog, derivative, or salt thereof. This would include, for example, but in no way limited to, the substances described in Table 1 herein. This would include, for example, a compound(s) that may bind to and activate a nicotinic cholinergic receptor (nAChR). This would also include, for example, a compound(s) and/or composition that modulates the signaling pathway, either upstream or downstream, that is activated by the binding of an activating ligand (such as nicotine and acetylcholine) to heteromeric and/or homomeric nAChRs. FIG. 11 herein depicts an overview of a signaling pathway of the α7 nAChR subtype. "Nicotinic receptor agent," for example, would include any of the compounds depicted in FIG. 11, such that they may modulate the signaling cascade effect of nicotine or acetylcholine binding to the nAChR, including the inhibition of the phosphorylation of inhibitor of NF-κB (IκB), the downregulation of the activation of mitogen-activated protein kinases (MAPKs), inhibition of the release of intracellular Ca$^{2+}$ stores and the formation of a heterodimeric protein complex with Janus kinase 1 (JAK2), which activates signal transducer and activator of transcription 2 (STAT3), and the inhibition of pro-inflammatory cytokine release.

As used herein, "pumps" include but is not limited to osmotic minipumps.

As disclosed herein, the inventors show that nicotine significantly attenuates the magnitude of inflammation and autoimmune responses against the myelin antigens in a mouse model of EAE. In the peripheral immune system, nicotine inhibits the proliferation of autoreactive T cells and alters the cytokine profile of helper T cells. In the CNS, nicotine preferentially reduced the number of migrated CD11b$^+$ and CD11b$^+$CD45$^+$ microglial, downregulated the expression of MHC class II, CD80 and CD86 molecules on these cells. The results demonstrate that physiological immune mechanisms modulated by nicotine can be exploited for the treatment of inflammatory and autoimmune disorders in the CNS.

In one embodiment, the present invention provides a method of treating a disease and/or condition by administering a therapeutically effective amount of a composition comprising nicotine. In one embodiment, the present invention provides a method of treating a disease and/or condition in an individual by administering a nicotinic receptor agent to the individual. In another embodiment, the disease and/or condition is EAE. In another embodiment, the disease and/or condition is multiple sclerosis. In another embodiment, the present invention provides a method of treating CNS inflammation and/or autoimmunity by administering a therapeutically effective dosage of nicotinic receptor agent. In another embodiment, administering a therapeutically effective dosage of nicotinic receptor agent attenuates CNS inflammation and/or autoimmune responsiveness to myelin antigens. In another embodiment, the nicotinic receptor agent is administered by osmotic minipumps implanted subcutaneously. In another embodiment, the nicotinic receptor agent is administered intravenously by direct injection. In another embodiment, the nicotinic receptor agent includes nicotinic bitartrate. In another embodiment, a therapeutically effective dosage of nicotinic receptor agent is 13 mg of nicotine free base/kg/d administered to a mouse, or the human dosage equivalent. In another embodiment, the individual is a human. In another embodiment, the individual is a mouse.

As further disclosed herein, the inventors have developed various methods of modulating the magnitude of inflammatory and autoimmune response against neuroantigens by nicotine. In one embodiment, the nicotine can be used to suppress an immune response to autoantigen. In another embodiment, the immune response to autoantigen is in vivo. In another embodiment, the immune response to autoantigen is ex vivo. In another embodiment, the immune response to autoantigen is in vitro. In another embodiment, the suppression of an immune response to an autoantigen results in the treatment, amelioration and/or prevention of an autoimmune and/or inflammatory disorder. In another embodiment, the autoimmune and/or inflammatory disorder is of the central nervous system.

The present invention is also directed to a kit to prepare a nicotinic receptor agent, as well as the delivery of the nicotinic receptor agent to an individual, and may include an osmotic minipump, nicotine bitartrate, PBS, and combinations thereof. The kit is an assemblage of materials or components, including at least one of the inventive compositions. Thus, in some embodiments the kit contains a composition including a therapeutically effective dosage of nicotine, as described above.

The exact nature of the components configured in the inventive kit depends on its intended purpose. For example, some embodiments are configured for the purpose of delivering a therapeutically effective dosage of nicotine to mammalian subjects, such as, but not limited to, human subjects, farm animals, domestic animals, and laboratory animals. Other embodiments, for example, are configured for preparing a therapeutically effective dosage of nicotine to mammalian subjects, such as, but not limited to, human subjects, farm animals, domestic animals, and laboratory animals.

Instructions for use may be included in the kit. "Instructions for use" typically include a tangible expression describing the technique to be employed in using the components of the kit to effect a desired outcome, such as to prepare a nicotinic solution and/or deliver a therapeutically effective dosage of nicotinic receptor agent to treat an immunological disease. Optionally, the kit also contains other useful components, such as, diluents, buffers, pharmaceutically acceptable carriers, syringes, catheters, applicators, pipetting or measuring tools, bandaging materials or other useful paraphernalia as will be readily recognized by those of skill in the art.

The materials or components assembled in the kit can be provided to the practitioner stored in any convenient and suitable ways that preserve their operability and utility. For example the components can be in dissolved, dehydrated, or lyophilized form; they can be provided at room, refrigerated or frozen temperatures. The components are typically contained in suitable packaging material(s). As employed herein, the phrase "packaging material" refers to one or more physical structures used to house the contents of the kit, such as inventive compositions and the like. The packaging material is constructed by well known methods, preferably to provide a sterile, contaminant-free environment. As used herein, the term "package" refers to a suitable solid matrix or material such as glass, plastic, paper, foil, and the like, capable of holding the individual kit components. Thus, for example, a package can be a glass vial used to contain suitable quantities of an inventive composition containing a solution of nicotine or components thereof. The packaging material generally has an external label which indicates the contents and/or purpose of the kit and/or its components.

In various embodiments, the present invention provides pharmaceutical compositions including a pharmaceutically acceptable excipient along with a therapeutically effective amount of nicotine. "Pharmaceutically acceptable excipient" means an excipient that is useful in preparing a pharmaceutical composition that is generally safe, non-toxic, and desirable, and includes excipients that are acceptable for veterinary use as well as for human pharmaceutical use. Such excipients may be solid, liquid, semisolid, or, in the case of an aerosol composition, gaseous.

In various embodiments, the pharmaceutical compositions according to the invention may be formulated for delivery via any route of administration. "Route of administration" may refer to any administration pathway known in the art, including but not limited to an osmotic minipump, intravenous injection, aerosol, nasal, oral, transmucosal, transdermal or parenteral. "Parenteral" refers to a route of administration that is generally associated with injection, including intraorbital, infusion, intraarterial, intracapsular, intracardiac, intradermal, intramuscular, intraperitoneal, intrapulmonary, intraspinal, intrasternal, intrathecal, intrauterine, intravenous, subarachnoid, subcapsular, subcutaneous, transmucosal, or transtracheal. Via the parenteral route, the compositions may be in the form of solutions or suspensions for infusion or for injection, or as lyophilized powders.

The nicotinic receptor agents according to the invention can also contain any pharmaceutically acceptable carrier. "Pharmaceutically acceptable carrier" as used herein refers to a pharmaceutically acceptable material, composition, or vehicle that is involved in carrying or transporting a compound of interest from one tissue, organ, or portion of the body to another tissue, organ, or portion of the body. For example, the carrier may be a liquid or solid filler, diluent, excipient, solvent, or encapsulating material, or a combination thereof. Each component of the carrier must be "pharmaceutically acceptable" in that it must be compatible with the other ingredients of the formulation. It must also be suitable for use in contact with any tissues or organs with which it may come in contact, meaning that it must not carry a risk of toxicity, irritation, allergic response, immunogenicity, or any other complication that excessively outweighs its therapeutic benefits.

The nicotinic receptor agents according to the invention can also be encapsulated, tableted or prepared in an emulsion or syrup for oral administration. Pharmaceutically acceptable solid or liquid carriers may be added to enhance or stabilize the composition, or to facilitate preparation of the composition. Liquid carriers include syrup, peanut oil, olive oil, glycerin, saline, alcohols and water. Solid carriers include starch, lactose, calcium sulfate, dihydrate, terra alba, magnesium stearate or stearic acid, talc, pectin, acacia, agar or gelatin. The carrier may also include a sustained release material such as glyceryl monostearate or glyceryl distearate, alone or with a wax.

The preparations of nicotinic receptor agents are made following the conventional techniques of pharmacy involving milling, mixing, granulation, and compressing, when necessary, for tablet forms; or milling, mixing and filling for hard gelatin capsule forms. When a liquid carrier is used, the preparation will be in the form of a syrup, elixir, emulsion or an aqueous or non-aqueous suspension. Such a liquid formulation may be administered directly p.o. or filled into a soft gelatin capsule.

The nicotinic receptor agents according to the invention may be delivered in a therapeutically effective amount. The precise therapeutically effective amount is that amount of the composition that will yield the most effective results in terms of efficacy of treatment in a given subject. This amount will vary depending upon a variety of factors, including but not limited to the characteristics of the therapeutic compound (including activity, pharmacokinetics, pharmacodynamics, and bioavailability), the physiological condition of the subject (including age, sex, disease type and stage, general physical condition, responsiveness to a given dosage, and type of medication), the nature of the pharmaceutically acceptable carrier or carriers in the formulation, and the route of administration. One skilled in the clinical and pharmacological arts will be able to determine a therapeutically effective amount through routine experimentation, for instance, by monitoring a subject's response to administration of a compound and adjusting the dosage accordingly. For additional guidance, see *Remington: The Science and Practice of Pharmacy* (Gennaro ed. 20th edition, Williams & Wilkins PA, USA) (2000).

Typical dosages of nicotinic receptor agents can be in the ranges recommended by the manufacturer where known therapeutic compounds are used, and also as indicated to the skilled artisan by the in vitro responses or responses in animal models. Such dosages typically can be reduced by up to about one order of magnitude in concentration or amount without losing the relevant biological activity. Thus, the actual dosage will depend upon the judgment of the physician, the condition of the patient, and the effectiveness of the therapeutic method based, for example, on the in vitro responsiveness of the relevant primary cultured cells or histocultured tissue sample, such as the responses observed in the appropriate animal models, as previously described. In one embodiment, a therapeutically effective dosage of nicotinic receptor agent administered to a mouse ranges from 1 mg nicotine free base/kg/day to 60 mg nicotine free base/kg/day, with a preferable dosage of 13 mg nicotine free base/kg/day. In another embodiment, a therapeutically effective dosage of nicotinic receptor agent administered to a human ranges from nicotine plasma levels of 1 ng/mL to 100 ng/mL, with a preferable dosage of 30 ng/mL. In another embodiment, a therapeutically effective dosage of nicotinic receptor agent administered to a human as a single dose ranges from 0.1 mg to 5 mg, with 1 mg the preferred single dose. In another embodiment, a therapeutically effective dosage of nicotinic receptor agent administered to a human ranges from 0.015 mg/kg/day to 0.6 mg/kg/day, with a preferable dosage of 0.3 mg/kg/day.

As described herein, various embodiments of the invention include the attenuation of CNS inflammation and autoimmune responsiveness to antigens. As readily apparent to one of skill in the art, the invention may be applied to any number of CNS conditions and diseases, including stroke, trauma, Alzheimer's disease, Parkinson's disease, epilepsy, encephalomyelitis and MS.

Additionally, as would be readily apparent to one of skill in the art, any number of methods and devices commercially available may be used, either alone or in conjunction with various embodiments described herein, to deliver a therapeutically effective dosage of nicotinic receptor agent, and the invention is in no way limited to intravenous delivery by injection or through subcutaneous implantation of osmotic minipumps. This would include, but not limited to, nasal sprays, oral nicotine, nicotine patches, nicotine gum, and nicotine inhalers. Additionally, as readily apparent to one of skill in the art, there are any number of nicotinic compounds, either alone or in conjunction with various embodiments described herein, that could be used for the delivery of a therapeutically effective dosage of nicotinic receptor agent, and the invention is in no way limited to use of nicotine bitartrate. This would include, but not limited to, nicotine mimetics. Similarly, nicotine exposure-induced decreases in nicotinic receptor function may also have a therapeutic effect. This would include, but not limited to, agents or their analogs such as bupropion or mecamylamine, and non-competitive antagonists of nicotinic receptor subtypes or competitive inhibitors such as methyllycaconitine.

Similarly, as readily apparent to one of skill in the art, the invention may also be used in the form of adjuvant therapies. In one embodiment, a disease may be treated by administering a therepeutically effective dosage of a nicotinic receptor agent in conjunction with administering a thereapeutically effective dosage of a composition, where a condition associated with the disease is treated by administering the nicotinic receptor agent, and the disease itself is treated by administering the composition. In one embodiment, the condition associated with the disease is CNS inflammation. In another embodiment, the disease is a neurodegenerative disease. In another embodiment, the disease is stroke, trauma, Alzheimer's disease, Parkinson's disease, and/or epilepsy. In another embodiment, the condition associated with the disease is an autoimmune effect. In another embodiment, the disease is HIV/AIDS, lupus, encephalomyelitis and/or MS.

One skilled in the art will recognize many methods and materials similar or equivalent to those described herein, which could be used in the practice of the present invention. Indeed, the present invention is in no way limited to the methods and materials described. For purposes of the present invention, the following terms are defined below.

EXAMPLES

The following examples are provided to better illustrate the claimed invention and are not to be interpreted as limiting the scope of the invention. To the extent that specific materials are mentioned, it is merely for purposes of illustration and is not intended to limit the invention. One skilled in the art may develop equivalent means or reactants without the exercise of inventive capacity and without departing from the scope of the invention.

Example 1

Generally

The expression of nicotinic acetylcholine receptors in the non-neuronal cells, microglia and astrocytes, is evidence that the nicotinic receptor activity is involved in immune responses within the central nervous system (CNS). The inventors show that nicotine significantly attenuates the magnitude of inflammation and autoimmune responses against the myelin antigens in a mouse model of experimental autoimmune encephalomyelitis (EAE). In the peripheral immune system, nicotine inhibits the proliferation of autoreactive T cells and alters the cytokine profile of helper T cells. In the CNS, nicotine preferentially reduced the number of migrated $CD11b^+$ and $CD11b^+CD45^+$ microglia, and down-regulated the expression of MHC class II, CD80 and CD86 molecules on these cells. Results described herein show that physiological immune mechanisms modulated by nicotine can be exploited for the treatment of inflammatory and autoimmune disorders in the CNS.

Example 2

Mice

B6 $H-2^b$) mice purchased from Taconic (Germantown, N.Y., USA) were housed in pathogen-free animal facilities of the Barrow Neurological Institute, Phoenix, Ariz. The female mice used were 7 to 8 weeks of age at the experiment's inception. Experiments were conducted in accordance with institutional guidelines.

Example 3

Antigens

The murine $MOG_{35-55}$ peptide (SEQ. ID. NO.: 1) and proteolipid protein $(PLP)_{139-151}$ peptide (SEQ. ID. NO.: 2) were synthesized by Bio Synthesis Inc. (Lewisville, Tex., USA).

Example 4

Induction of Acute EAE and Adoptive Transfer of EAE

To induce acute EAE, B6 mice were injected subcutaneously (s.c.) in the hind flank with 200 µg of $MOG_{35-55}$ peptide in complete Freund's adjuvant (CFA) (Difco, Detroit, Mich., USA) containing 500 µg of mycobacterium tuberculosis. On the day of immunization and 2 days afterward, the mice were injected intraperitoneally (i.p.) with 200 ng pertussis toxin (List Biologic, Campbell, Calif., USA).

For adoptive transfers of EAE, lymph node cells were obtained from these mice on day 8 after immunization and cultured at a density of $2 \times 10^6$/ml in Click's EHAA medium supplemented with 15% FCS, 20 ng/ml recombinant IL-12, and 50 µg/ml $MOG_{35-55}$ peptide. After 4 days of culture, cells were harvested, and $3 \times 10^7$ viable cells were injected i.p. into each recipient mouse irradiated (350 rads) 1 h earlier. For both actively and passively induced EAE, the mice were observed daily for clinical signs of disease and scored on an arbitrary scale of 0 to 5, with gradations of 0.5 for intermediate scores: 0, no clinical signs; 1, flaccid tail; 2, hind limb weakness or abnormal gait; 3, complete hind limb paralysis; 4, complete hind limb paralysis with forelimb weakness or paralysis; 5, moribund or deceased.

Example 5

Nicotine Treatment

Nicotine bitartrate was purchased from Sigma (St. Louis, Mo., USA). A 100 mg/ml solution of nicotine bitartrate in phosphate-buffered saline (PBS) was freshly prepared 24 h before pump implantation. The solution was loaded into Alzet® osmotic minipumps (model 1007D, Durect Corporation, Cupertino, Calif., USA); the delivery rate is 12 µl/d or 0.39 mg/mouse/d. For a mouse approximately 30 gm, this equates to 13 mg of nicotine free base/kg/d or approximately 0.54 mg of nicotine free base/kg/hr. These minipumps were then implanted s.c. into the mice to continuously deliver nicotine or PBS for 7 days. Control mice received PBS via minipumps or direct injections, both of which produced identical results, as described herein.

To determine the ability of nicotine pretreatment to prevent an autoimmune response, mice received 13 mg/kg nicotine or PBS daily for a total of 7 doses starting on the day of MOG immunization to induce EAE (day 0) or 7 days earlier. To evaluate the effect of nicotine on an ongoing autoimmune response, mice received 13 mg/kg nicotine or PBS daily for a total of 7 doses on day 7 after EAE induction. For adoptive transfer of EAE, lymphocytes were isolated from mice that were treated with nicotine at a dose of 13 mg/kg or PBS daily for a total of 7 doses at the time of MOG immunization.

Example 6

Preparation of Tissues and Histological Staining

Mice were anesthetized with pentobarbital and perfused by intracardiac puncture with 50 ml of cold PBS. Spinal cords were removed and fixed in 10% formal in/PBS. Paraffin-embedded longitudinal sections were prepared and stained for hematoxylin and eosin (H&E), luxol fast blue (LFB, myelin staining) and Biechowsky silver (axon staining). The percentages of spinal cord inflammation, demyelination and axonal damage per mouse were calculated by first determining the total white matter area for all spinal cord sections by manually tracing the regions. Next, the areas of spinal cord inflammation, demyelination and axonal damage were determined by manually tracing each section. Pathological changes in each spinal cord were scored as follows: 0 no changes; 1 focal area involvement; 2<5% of total myelin area involved; 3 5-10% of total myelin area involved; 4 10-20% involved area; 5>20% of total myelin area involved (Bai, X. F., et al., *J Exp Med* 200:447-458).

Example 7

T Cell Proliferation Assays

Spleen mononuclear cells were suspended in culture medium containing Dulbecco's modification of Eagle's medium (Gibco, Paisley, UK) supplemented with 1% (v/v) minimum essential medium (Gibco), 2 mM glutamine (Flow Laboratory, Irvine, Calif., USA) 50 IU/ml penicillin, 50 mg/ml streptomycin and 10% (v/v) FCS (both from Gibco). Spleen mononuclear cells ($4 \times 10^5$ cells/well) in 200 µl of culture medium were placed in 96-well round-bottom microtiter plates (Nunc, Copenhagen, Denmark). Ten µl of $MOG_{35-55}$ peptide (10 µg/ml), $PLP_{139-151}$ peptide (10 µg/ml) or ConA (5 µg/ml) (Sigma-Aldrich, St Louis. Mo., USA) were then added into triplicate wells. After 3 days of incubation, the cells were pulsed for 18 h with 10 µl aliquots containing 1 µCi of $^3$H-methylthymidine (sp. act. of 42 Ci/mmo; MP Biomedicals, Irvine, Calif., USA). Cells were harvested onto glass fiber filters, and thymidine incorporation was then measured. The results were expressed as counts per minute (cpm).

Single cell suspensions ($4 \times 10^7$ cells) were prepared and labeled with 0.5 µM CFSE at 37° C. for 10 min. Cells with or without CFSE were incubated at 37° C. for 3 days in round-bottom plates ($2 \times 10^6$ cells/well) with or without antigens (MOG 10 µg/ml). After harvesting, cells were stained for surface markers with fluorochrome-conjugated monoclonal antibodies including anti-CD3-PE/Cy5 (17A2), anti-CD4-APC/Cy7 (GK1.5), and anti-CD8α-PE/Cy7 (53-6.7) (BD Bioscience, San. Diego, Calif., USA). Isotype-matched negative monoclonal antibodies were used as controls.

Example 8

Cell Viability and Apoptosis Assay

Cell viability was assessed by trypan blue dye exclusion. For detection of cell apoptosis, the spleen mononuclear cell suspensions were collected from PBS and nicotine-treated mice on day 11 (peak stage). Single cell suspensions were washed in PBS and resuspended in binding buffer containing annexin V-FITC and propidium iodide (PI) (both from BD Biosciences) for 20 min at room temperature. The samples were analyzed on a FACSAria using Diva.

Example 9

Spleen and CNS Cell Isolation and Flow Cytometric Analysis

Spleen mononuclear cell suspensions were collected from PBS and nicotine-treated mice on day 11 (peak stage). Single cell suspensions were prepared and stained with fluorescently labeled antibodies to mouse antigens. Antibodies were directly labeled with one of the following fluorescent tags: FITC, PE, APC, PF-Cy5, PE-Cy-7, CD25 (PC61.5), APC-Cy7; CD3 (17A2), CD4 (GK1.5), CD8 (53-6.7). NK1.1

(PK136), CD11b (M1/70), CD11c (HL3), CD19 (1D3). CD80 (16-10A1), CD86 (GL1), MAC class II (M5/1 14.15), and TCRβ (H57-597). Intracellular Foxp3 (FJK-16s) cells were stained as the manufacture instructed (eBioscience, San Diego, Calif., USA). Appropriate isotype controls were always included. All samples were analyzed on a FACSAria using Diva. The absolute number of a particular cell subset was calculated by counting the mean of total mononuclear cells isolated per mouse spleen and multiplying by the percentage of those cells acquired by FACSAria flow cytometry.

For CNS cell isolates, at day 11 after EAE induction (peak stage), mice were sacrificed and perfused with PBS through the left heart ventricle to eliminate contaminating blood cells in the CNS. The CNS mononuclear cells were then isolated from five to six mice using Percoll gradients and stained for cell surface markers. Antibodies were directly labeled and analyzed as done for splenocytes. The absolute number of a particular cell subset was calculated by counting the total number of mononuclear cells isolated from the CNS of individual mice and multiplying by the percentage of those cells acquired by FACSAria flow cytometry (Bai, X. F., et al., *J Exp Med* 200:447-458).

Example 10

Cytokine Quantification

Single cell suspensions ($4 \times 10^7$ cells) were prepared and incubated at 37° C. for 3 days in round-bottom plates ($2 \times 10^6$ cells/well) with or without antigens (MOG 10 µg/ml, PLP 10 µg/ml or Con A 2.5 µg/ml), and stimulated with PMA (20 ng/ml)/ionomycin (1 µg/ml)/brefeldin A (5 µg/ml) for another 5 h at 37° C. After harvesting, cells were stained for surface markers with fluorochrome-conjugated monoclonal antibodies including anti-CD3-PE/Cy5 (17A2), anti-CD4-APC/Cy7 (GK1.5), and anti-CD8α-PE/Cy7 (53-6.7) (BD Bioscience). Isotype-matched negative monoclonal antibodies were used as controls. For intracellular cytokine staining, after fixation and permeabilization with Cytofix/Cytoperm kit (BD Bioscience), anti-IFN-γ, anti-IL-10 and anti-IL-17 monoclonal antibody conjugated with Alexa 647 were used. All samples were analyzed on a FACSAria using Diva. To determine the percentage of cells producing cytokine, the value obtained with the isotype control was subtracted from that with specific antibody. For cytokine induction, supernatants were collected 3 days after in vitro boosting. IFN-γ, IL-10, IL-2 and TGF-β were measured by optEIA kits (PharMingen and eBioscience).

Example 11

Quantification of MOG-Reactive Antibodies

MOG-reactive antibodies were quantified by enzyme-linked immunoabsorbent assay (ELISA). Briefly, microtiter plates (Corning Glass Works, Corning, N.Y., USA) were coated with 100 µl/well of murine $MOG_{35-55}$ (10 µg/ml) at 4° C. overnight. After blocking with 10% fetal bovine serum, serum samples (day 11, peak stage after immunization) were added and incubated at 4° C. overnight. Plates were then incubated for 2 h with biotinylated rabbit anti-mouse IgG, IgG1, IgG2a, IgA, IgG3 and IgG2b (Invitrogen, Carlsbad, Calif. USA), followed by alkaline phosphatase-conjugated ABC reagent (Dakopatts; R&D systems, Minneapolis, Minn., USA). The color was developed with p-nitrophenyl-phosphate. Results were expressed as optical density (OD) at 450 nm.

Example 12

Statistical Analysis

Differences between groups were evaluated by ANOVA. The Fisher's exact test and Mann-Whitney's U-test were applied to analyze disease incidence and severity, respectively.

Example 13

Nicotinic Attenuation of Actively Induced-and Adoptively Transferred-EAE

To determine how nicotine might influence the course of EAE, B6 mice were infused with PBS or nicotine at a dose of 13 mg/kg for 7 days by using an implantable minipump. The decision on dosage and route of administration was based on recently published guidelines for testing the effects of nicotine in vivo (Matta, S. G., et al., *Psychopharmacology* (Berl) 190:269-319). The dosage applied in the study is estimated close to physiological dosage of nicotine.

A single injection of $MOG_{35-55}$ peptide together with CFA and pertusis toxin induced moderate to severe EAE (mean maximal clinical score 4.25±0.80, mean clinical score 2.99±0.67) in the majority of B6 mice tested. The average time of disease onset was 7.6±0.53 days post-immunization (p.i.). Ascending paralysis ensued at about 9 to 14 days, followed by some degree of recovery with a residual neurological deficit at the experiment's termination (mean clinical score 2.75±0.25) at day 30 p.i. In contrast, mice receiving nicotine prior to or the day of disease induction had a delayed onset of EAE, which was not apparent until day 10 p.i. Nicotine-treated groups developed EAE with mean maximal clinical scores of 3.13±0.25 (nicotine treatment group, starting day 0 after immunization) and 3.17±0.78 (pre-treatment group, starting day −7 after immunization). The latter's disease was significantly less severe than that of control mice given PBS, and the mean day of disease onset after nicotine treatment was clearly later than that of PBS controls ($p<0.01$). Nicotine treatment before or at the time of disease induction showed similar peak clinical scores and delayed onset of EAE ($p<0.05$, $p<0.01$, respectively, when compared with that of control animals). The disease of nicotine-treated mice was relatively mild, at maximum 3.13±0.25 vs. 4.25±0.80 ($p<0.01$). The majority of animal recovered by day 21 (nicotine pre-treated group) or 24 (nicotine-treated group) with a mild motor deficit remaining (mean clinical score 0.83±0.26, 0.85±0.25 vs. 2.75±0.25, $p<0.01$, respectively). Thus, nicotine exposure preceding or simultaneous with disease induction significantly delayed its onset, attenuated its severity and promoted the recovery.

Figure 1:
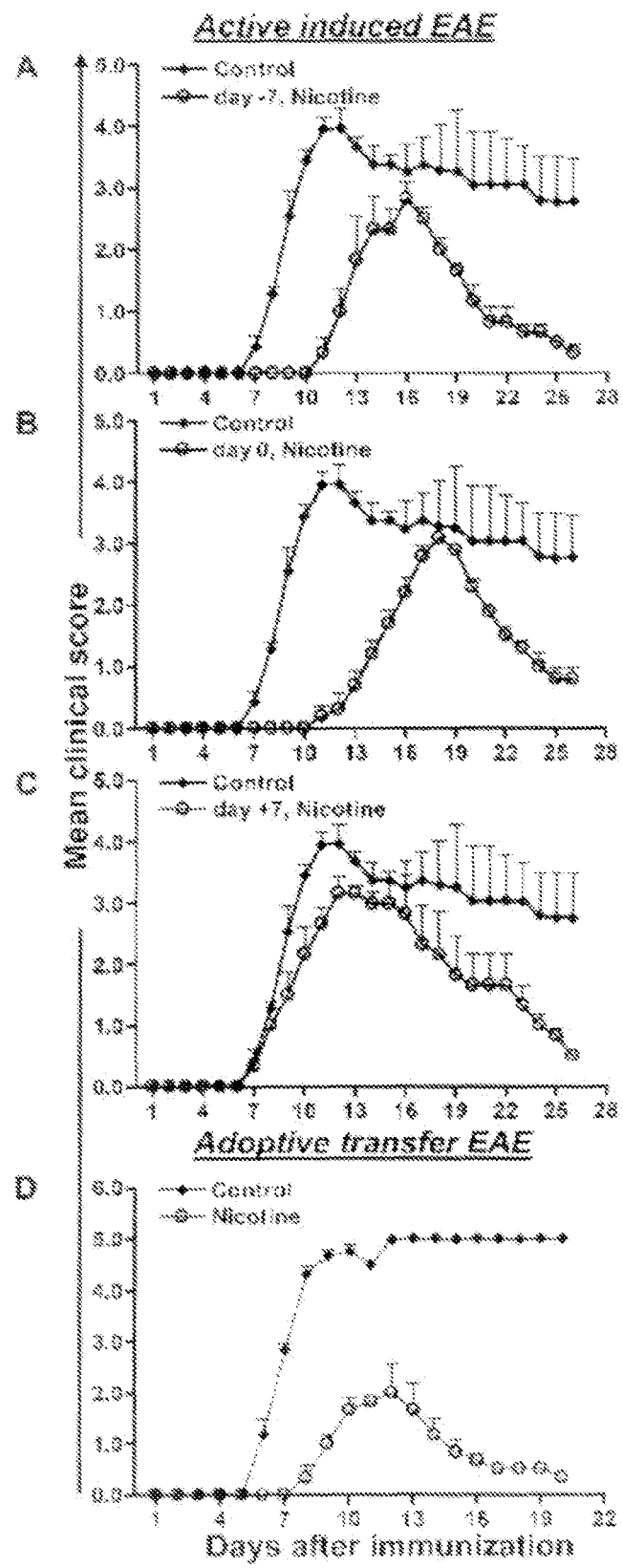
FIG. 1 depicts nicotinic attenuation of actively induced and adoptively transferred EAE Nicotine or PBS were administered at a dose of 13 mg/kg daily for a total of 7 doses, and treatment started at the indicated days (−7, A; 0, B; +7, C) The mice were observed daily and scored for clinical disease. Data represent mean±SD of total mice in each group (10 to 12 mice/group). Statistical evaluation was performed to compare experimental groups and corresponding control groups. Results for adoptively transferred EAE are illustrated in D (n=5 each group).
Figure 2:
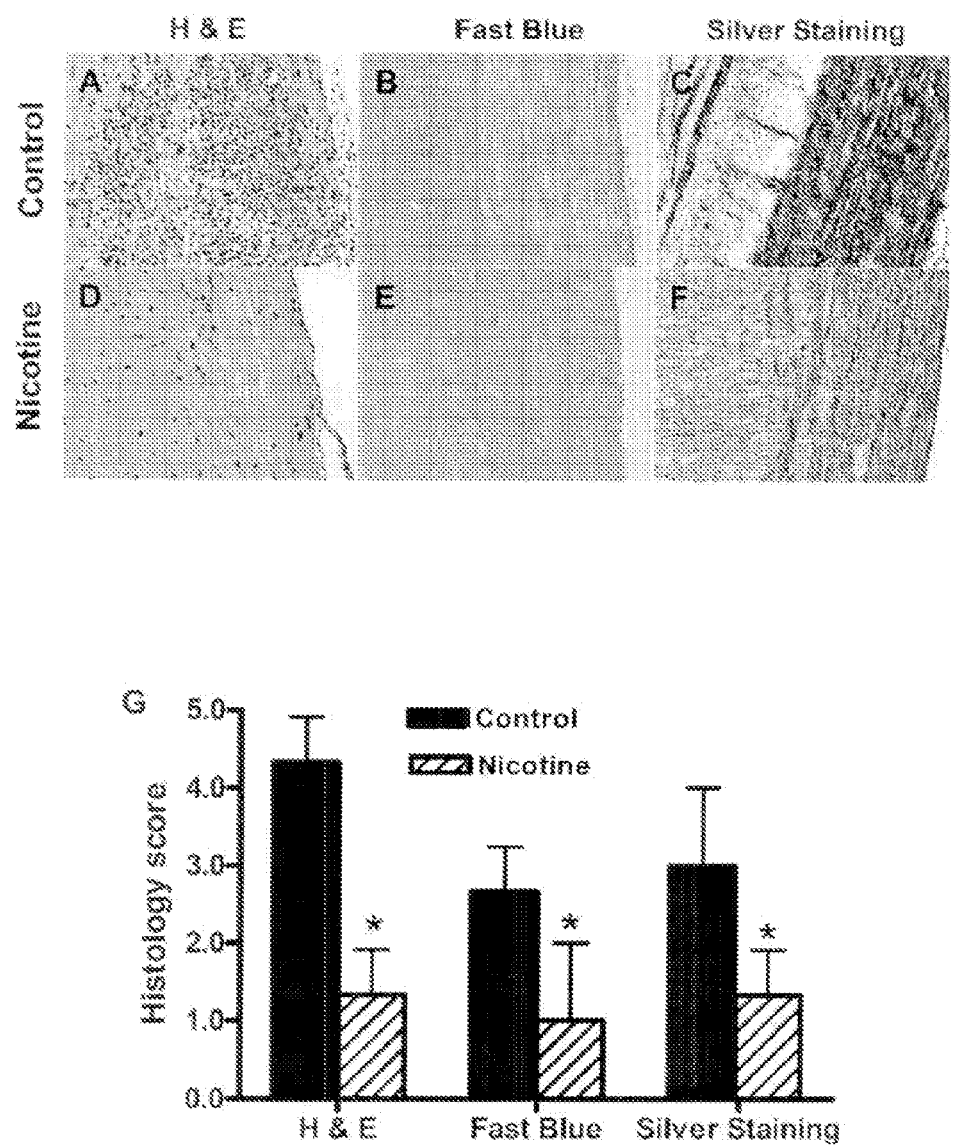
FIG. 2 depicts nicotine ameliorates CNS inflammation, demyelination and axonal damage. At day 25 p.i., mice were sacrificed, and CNS tissues were fixed in formalin then processed for staining with H&E (left panel), LFB (middle panel) or Biechowsky silver (right panel). A-C, control group. D-F, nicotine-treated group. Original photos were taken at 200×. G, Seminal quantitative summary of inflammation, demyelination and axonal damage. To calculate the extent of CNS pathology, the percentages of spinal cord inflammation, demyelination and axonal damage per mouse were calculated by first determining the total white matter area for all spinal cord sections by manually tracing the regions. Next the areas of spinal cord inflammation, demyelination and axonal damage were determined by manually tracing each section. Pathological changes of each spinal cord were scored as described herein. n=3 for all experiments. *P<0.05. Mann-Whitney U-test was used for the comparison.
Figure 3:
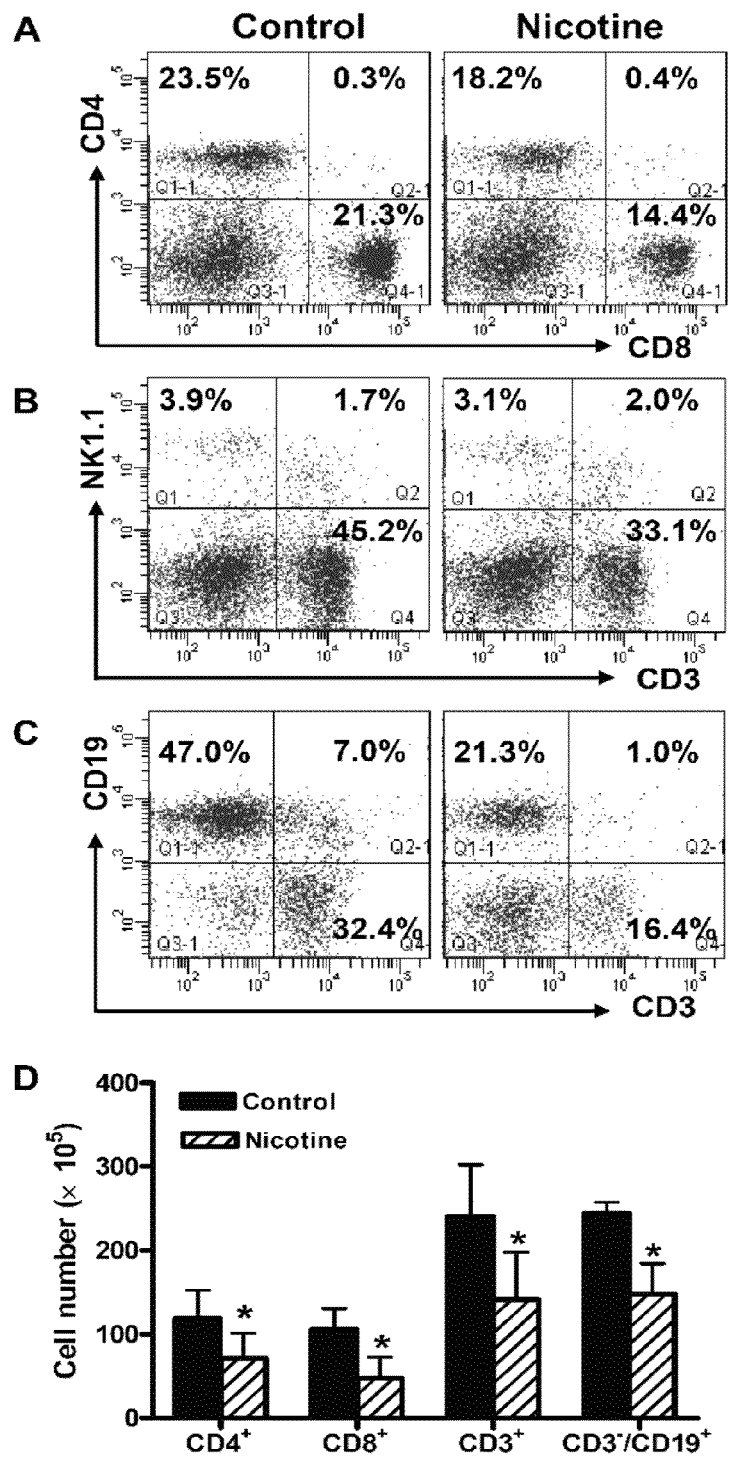
FIG. 3 depicts nicotine alters the peripheral lymphocyte subpopulation during EAE. On the day of immunization to incite acute EAE, mice were treated with nicotine at a dose of 13 mg/kg or PBS daily for a total of 7 doses. Mice were killed on day 11 after immunization, and mononuclear cells were isolated from their spleens as described herein. The dot plots generated after gating on lymphocytes (by forward vs. side scatter) are shown for T cells and B cells. A-C Representative dot plot results for CD4$^+$, CD8$^+$, NK, NKT cells, and CD3$^-$ CD19$^-$ cells. D. The absolute number of CD4$^+$, CD8$^+$, CD3$^+$, and CD3$^-$ CD19$^+$ cells. (n=5 mice each group). Data presented in FIGS. 4-8 were also generated using cells prepared at this time point.
Figure 4:
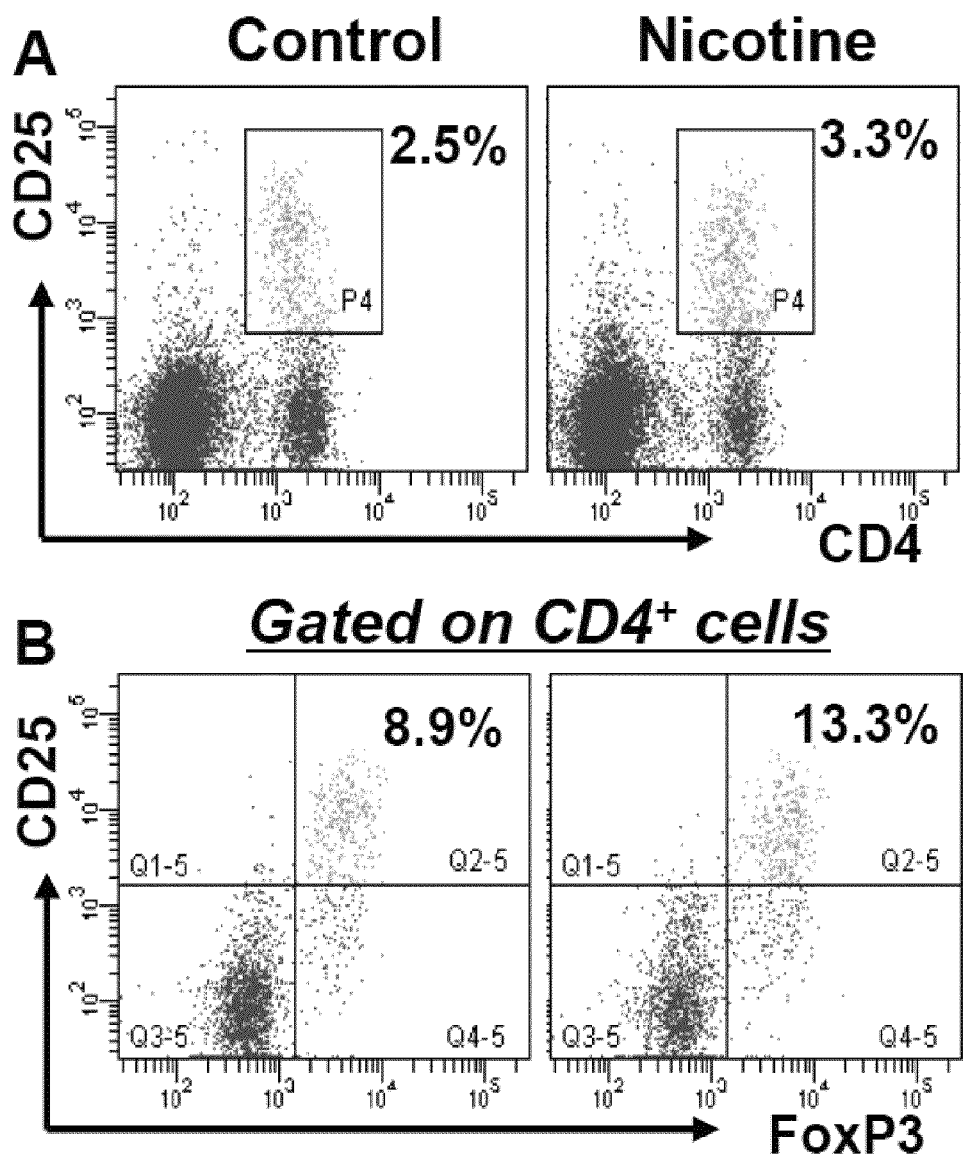
FIG. 4 depicts nicotine augments the expression of FoxP3 on regulatory T cells. A, Representative plots from individual mice showing the percentage of CD4$^+$CD25$^-$ T cells gated on lymphocytes (n=5). B, The expression of Foxp3 in relation to CD25$^+$ cells was determined by gating on CD4$^+$ cells (n=5). C, The average percentage of CD4$^+$CD25$^+$ T cells and Treg$^+$/FoxP3$^+$ cells in PBS- and nicotine-treated mice. The average percentage of Foxp3 and CD25 double positive cells was calculated by gating on CD4$^+$ cells in the PBS- and nicotine-treated mice.
Figure 4:
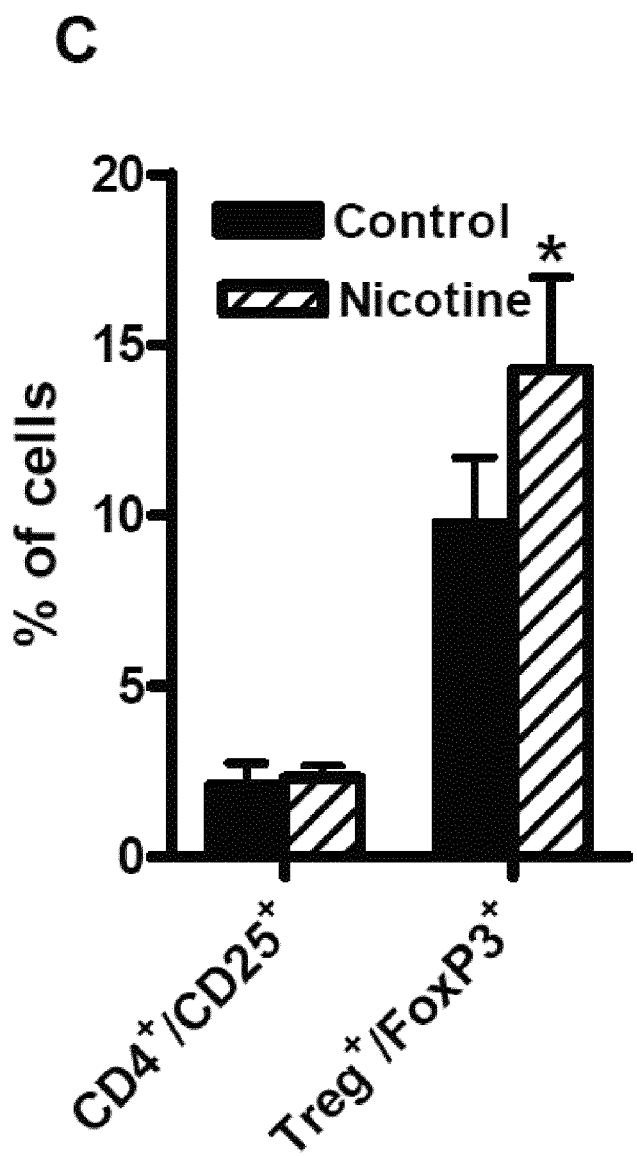
Figure 5C:
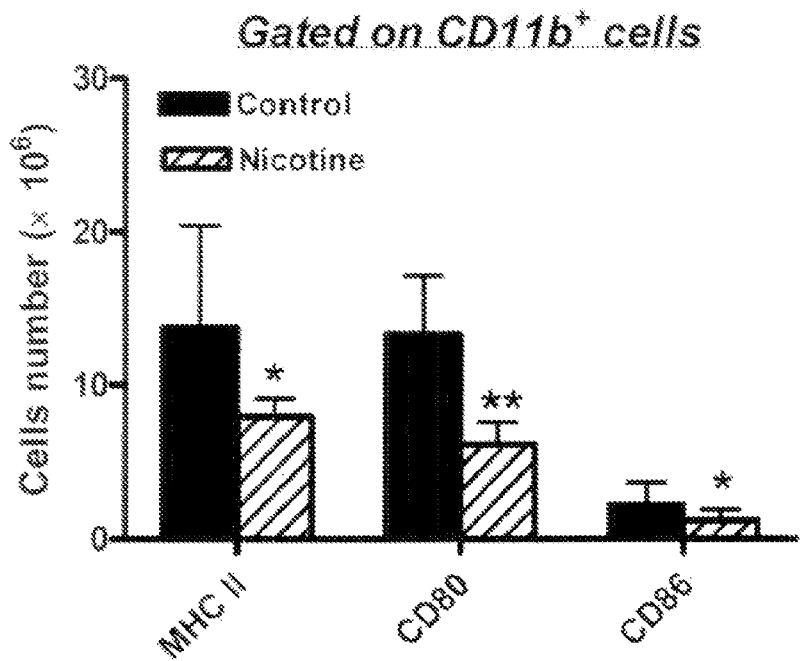
FIG. 5 depicts nicotine reduces the expression of MHC II, CD80, and CD86 on APCs in the periphery. A and C, MHC II, CD80 and CD86 expression was analyzed with gating on macrophages (CD11b$^+$) (representative histogram plots (A); absolute numbers (C)). B and D, MHC II, CD80, and CD86 expression was analyzed with gating on dendritic cells (CD11c$^+$) in the periphery (representative histogram plots (B); absolute numbers (D)). (n=5 mice each group). (*,p<0.05 vs. PBS, **, p<0.01 vs. PBS).
Figure 5D:
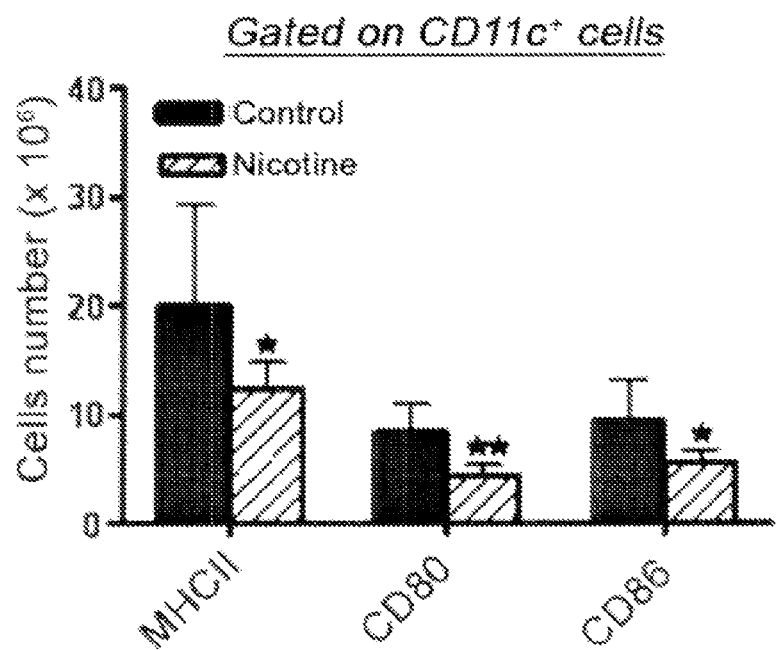
Figure 6:
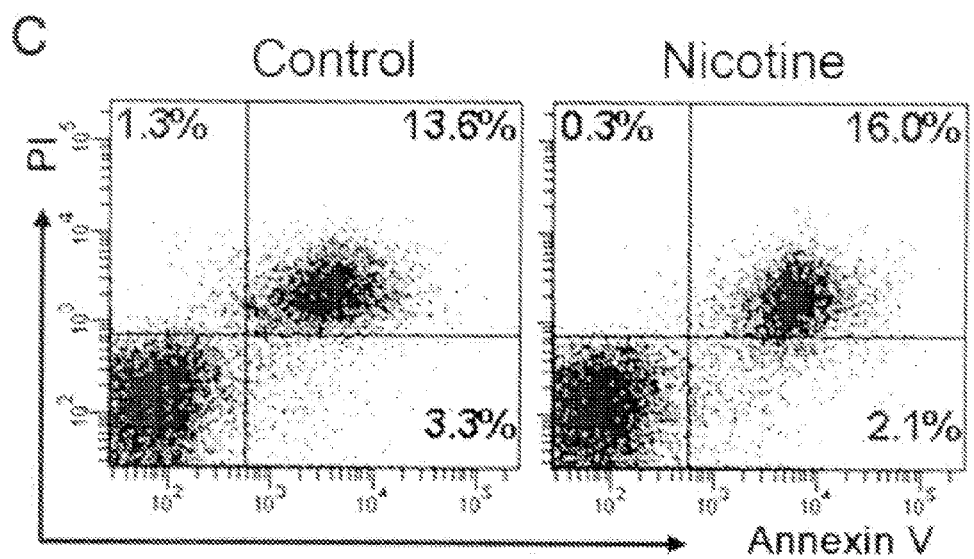
FIG. 6 depicts nicotine inhibits peripheral autoreactive T cell responses. A, The proliferation of antigen-specific splenic cells from PBS- or nicotine-treated mice was measured as $^3$H incorporation by these cells cultured with PLP or MOG. Results are expressed as mean cpm ±SD. B, Proliferation was assessed after CFSE staining of CD3$^+$ T cells, CD4$^+$ T cells, and CD8$^+$ T cells. C, Splenic cell apoptosis and death were detected by annexin V and PI double staining. Representative results from one of three independent experiments are shown (n=5 mice each group). (*,p<0.05 vs. PBS, **, p<0.01 vs. PBS).
Figure 7:
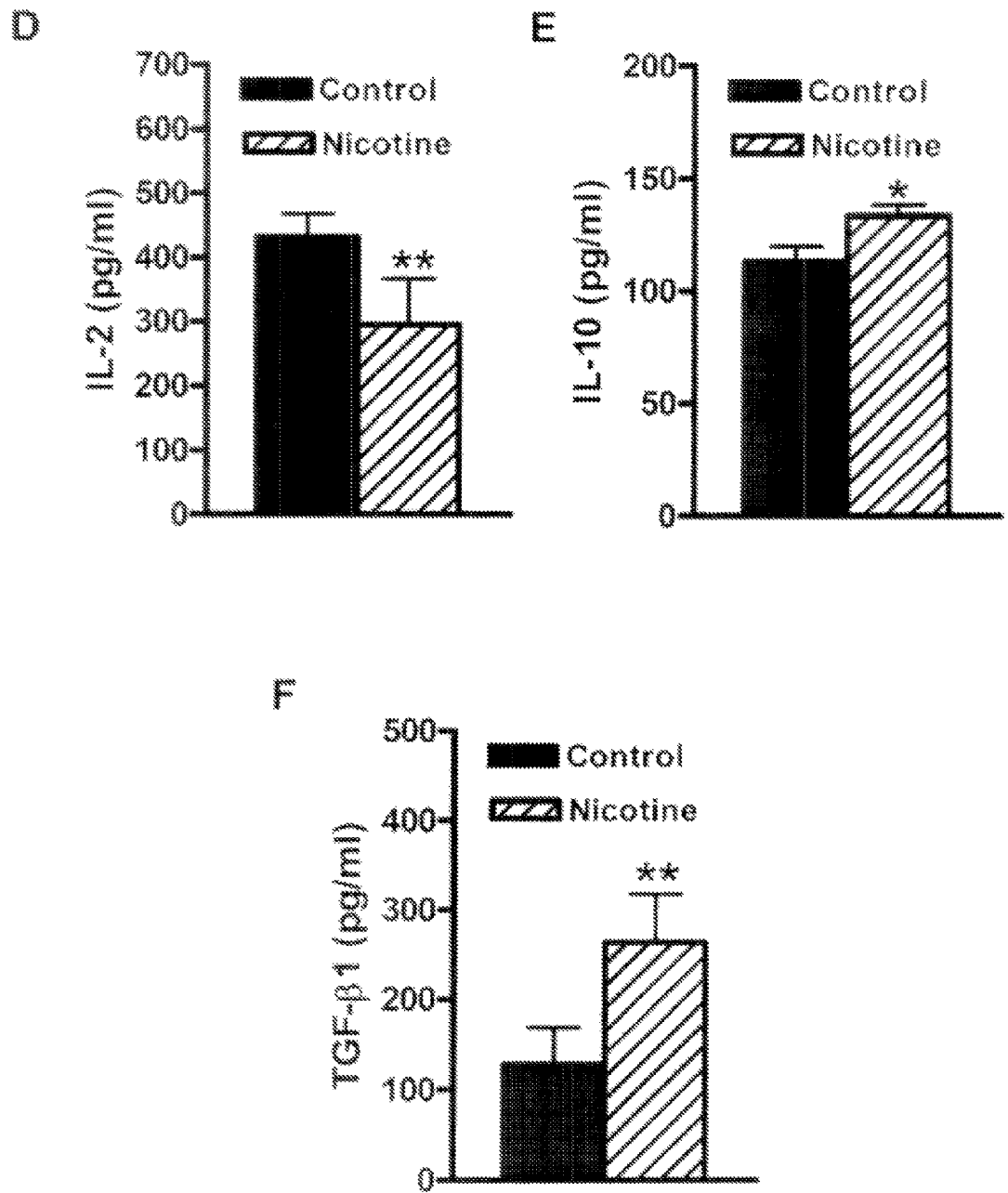
FIG. 7 depicts effects of nicotine on the Th response in. EAE mice. T cells were isolated from the groups of mice specified in FIG. 3 and cultured in the presence of MOG and other stimuli. Supernatants were harvested after 36 h, and IFN-γ (A), IL-2 (D), IL-10 (E) and TGF-β1 (F) production was determined by ELISA. B and C, IFN-γ secretion upon stimulation with MOG in nicotine- and PBS-treated mice was quantified by intracellular cytokine staining. B, Representative results appear in dot plots for CD4, CD8 and IFN-γ. C, The average percentage of CD4$^+$ IFN-γ$^+$ cells and CD8$^+$ IFN-γ$^+$ cells is shown. The data are means±SD of values from 9 mice per group.
Figure 8:
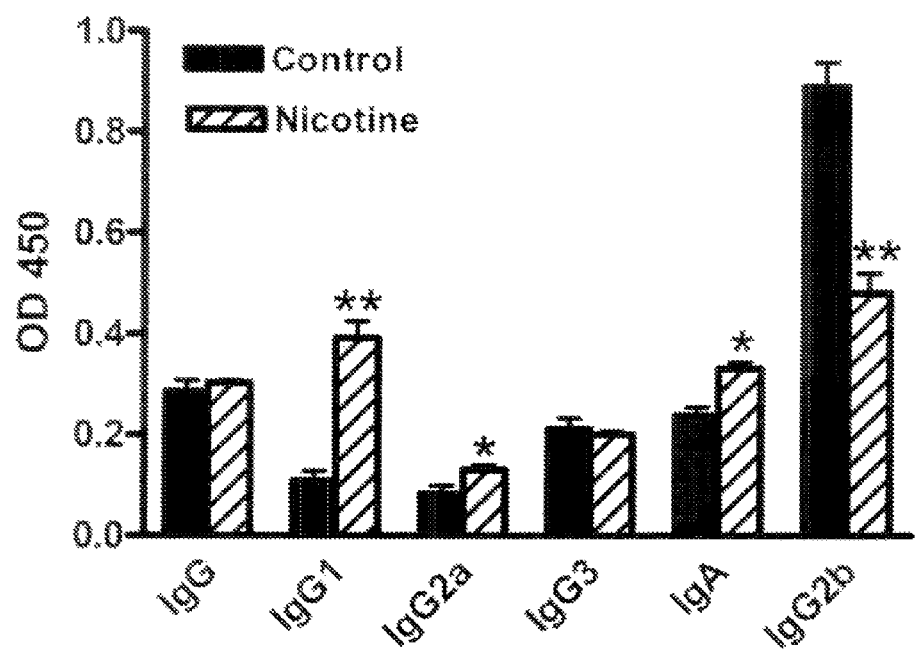
FIG. 8 depicts nicotine alters autoantibody isotypes. Sera were collected on day 11 after immunization, and the titers of MOG-specific IgG (1:500), IgG1 (1:500), IgG2b (1:500), IgG3 (1:100), IgA (1:100) and IgG2a (1:2) were determined by ELISA. Data are means±SD from three mice per group. Similar results were obtained in two independent experiments. (*,p<0.05 vs. PBS, * *, p<0.01 vs. PBS).
Figure 9:
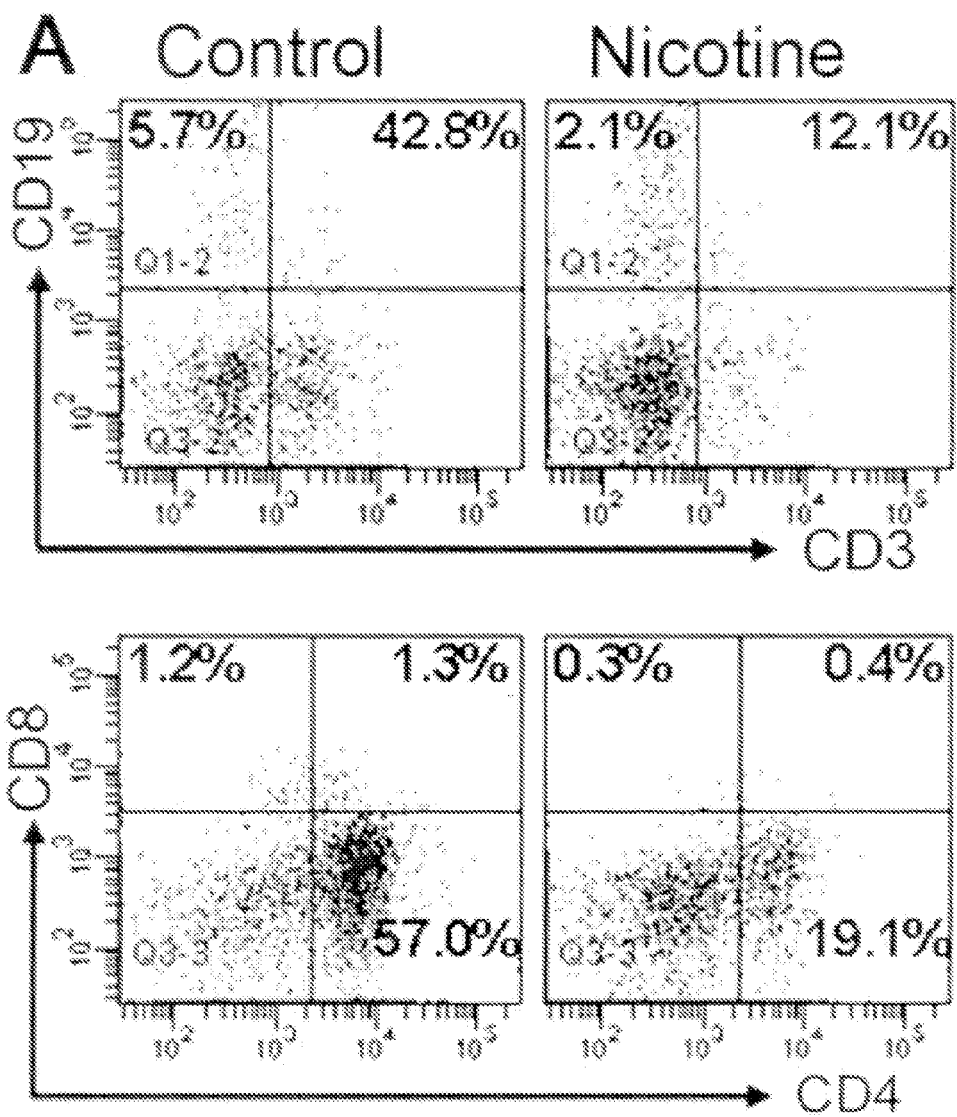
FIG. 9 depicts nicotine alters lymphocyte subpopulations in the CNS during EAE. On the day of immunization to incite acute EAE, mice were treated with nicotine at a dose of 13 mg/kg or PBS daily for a total of 7 doses. Mice were killed on day 11 after immunization, and mononuclear cells were isolated from the CNS. The dot plots generated after gating on mononuclear cells (by forward vs. side scatter) are shown for T cells and B cells. A, Representative dot plots are shown for CD3$^-$ CD19$^+$ cells (upper panel) and CD4$^+$ CD8$^+$ cells (lower panel).B, The Absolute numbers appear for CD3$^+$, CD3$^-$CD19$^+$, CD4$^-$, and CD8$^+$ cells.
Figure 9:
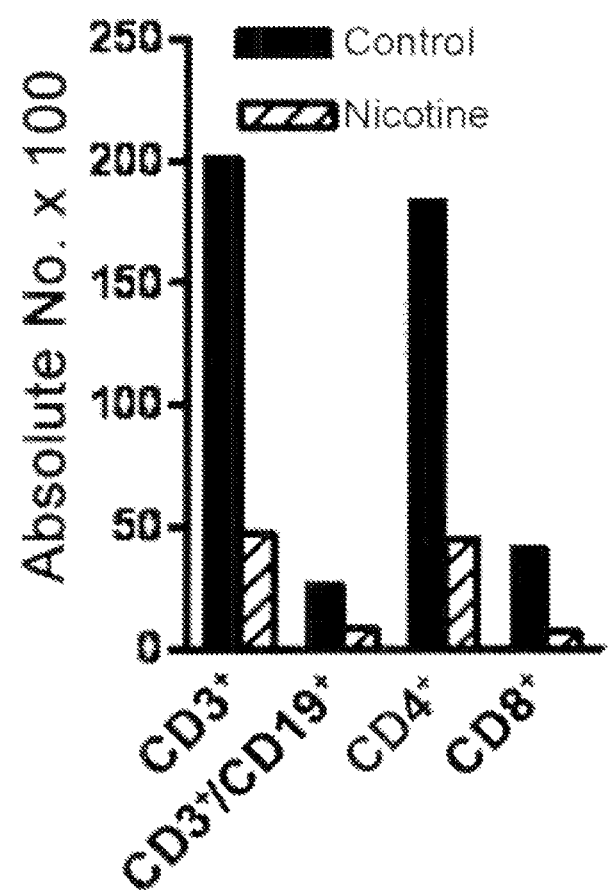
Figure 10:
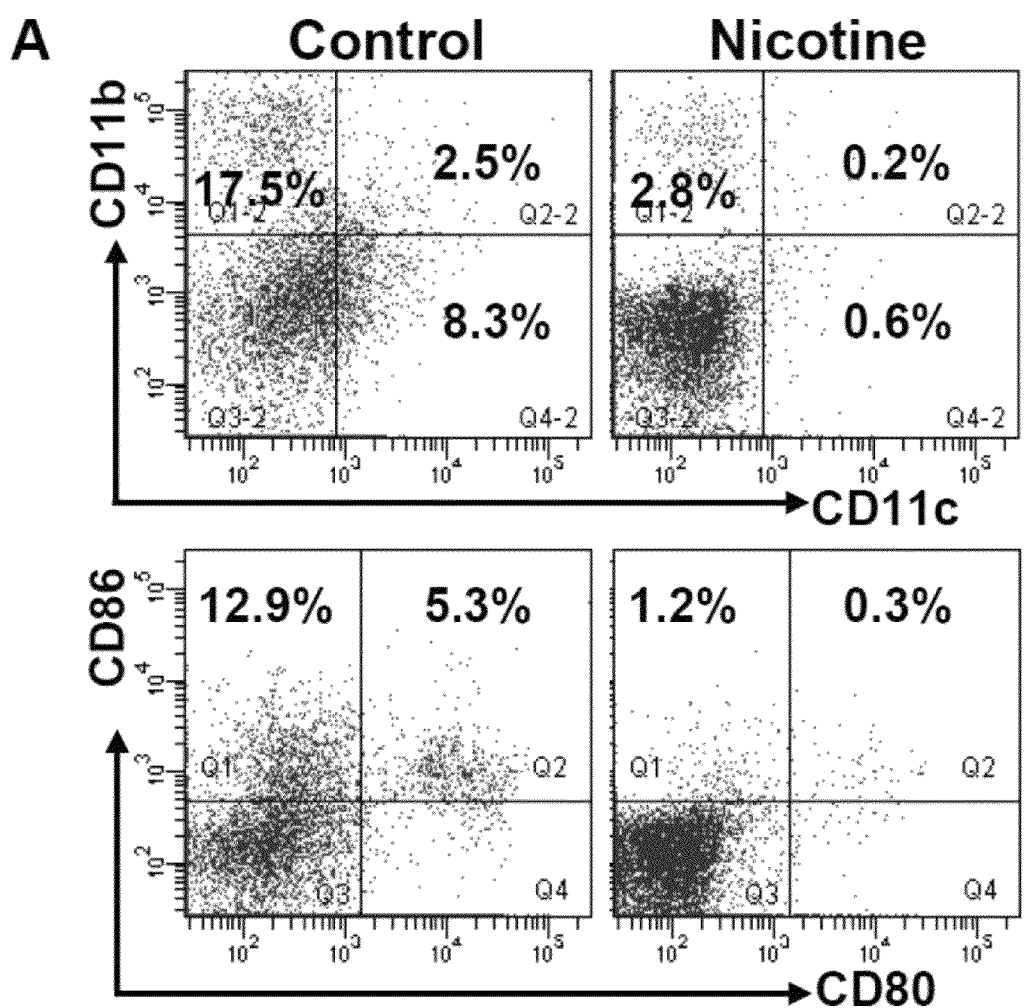
FIG. 10 depicts nicotine inhibits activation-induced MHC class II expression and suppresses co-stimulatory molecules in APCs. The mononuclear cells were isolated from CNS as in FIG. 9. A, The representative dot plot recapitulates results for dendritic cells (CD11b$^+$CD11c$^+$, upper panel) and co-stimulators (CD80$^+$/CD86$^+$, lower panel) on mononuclear cells. B, The absolute numbers of dendritic cells (CD11b$^+$CD11c$^+$) and co-stimulators (CD80$^+$/CD86$^+$) are also shown on mononuclear cells. C-D, MHC II, CD80 and, CD86 expression was analyzed by gating on live macrophages (CD11b$^+$) in the CNS (C are the representative histogram plots; D are the absolute numbers). E-F MHC II, CD80 and, CD86 expression was analyzed by gating on live dendritic cells (CD11c$^+$) in the CNS (E are the representative histogram plots; F are the absolute numbers). (*,p<0.05 vs. PBS, **,p<0.01 vs. PBS).
Figure 10:
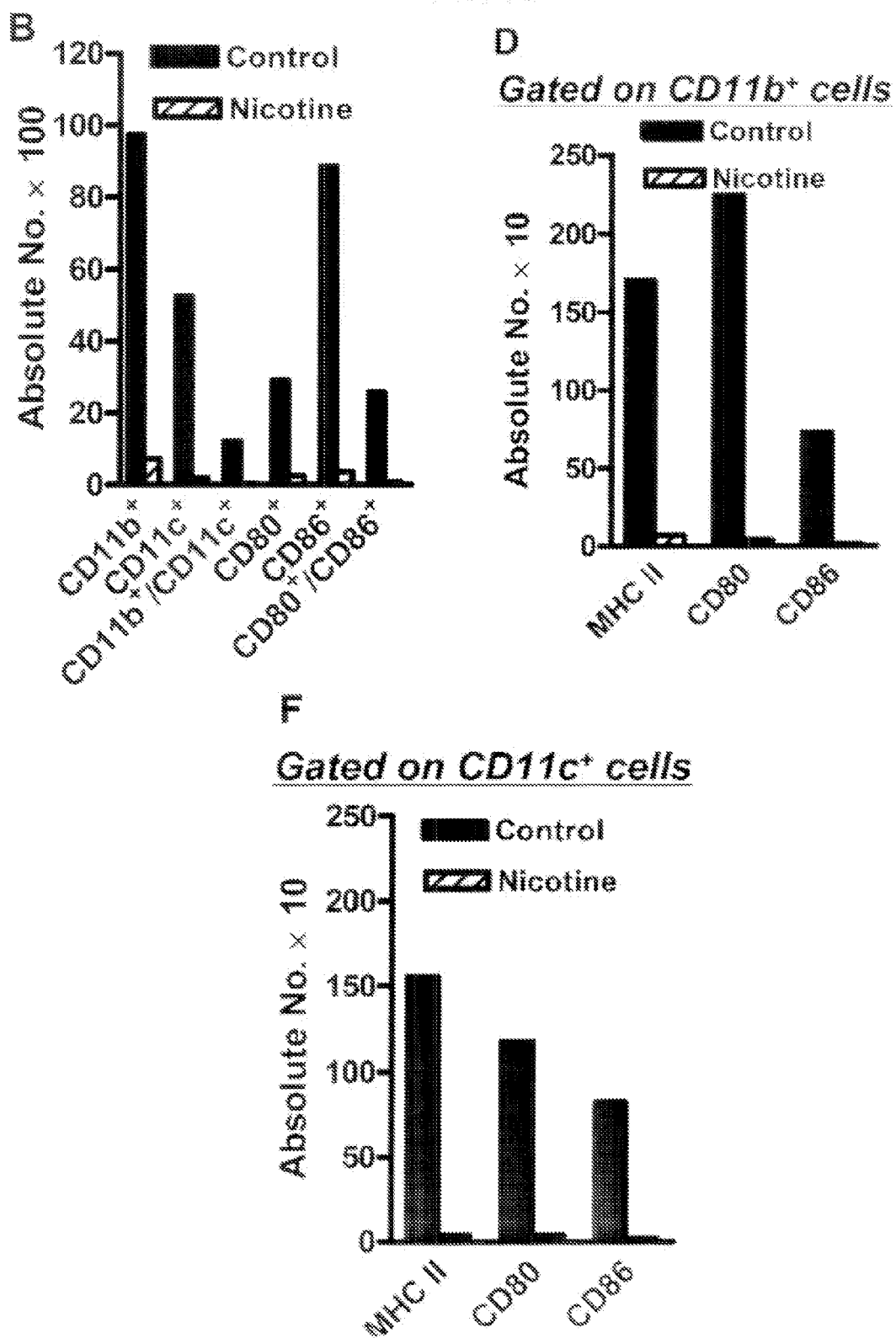
Figure 10:
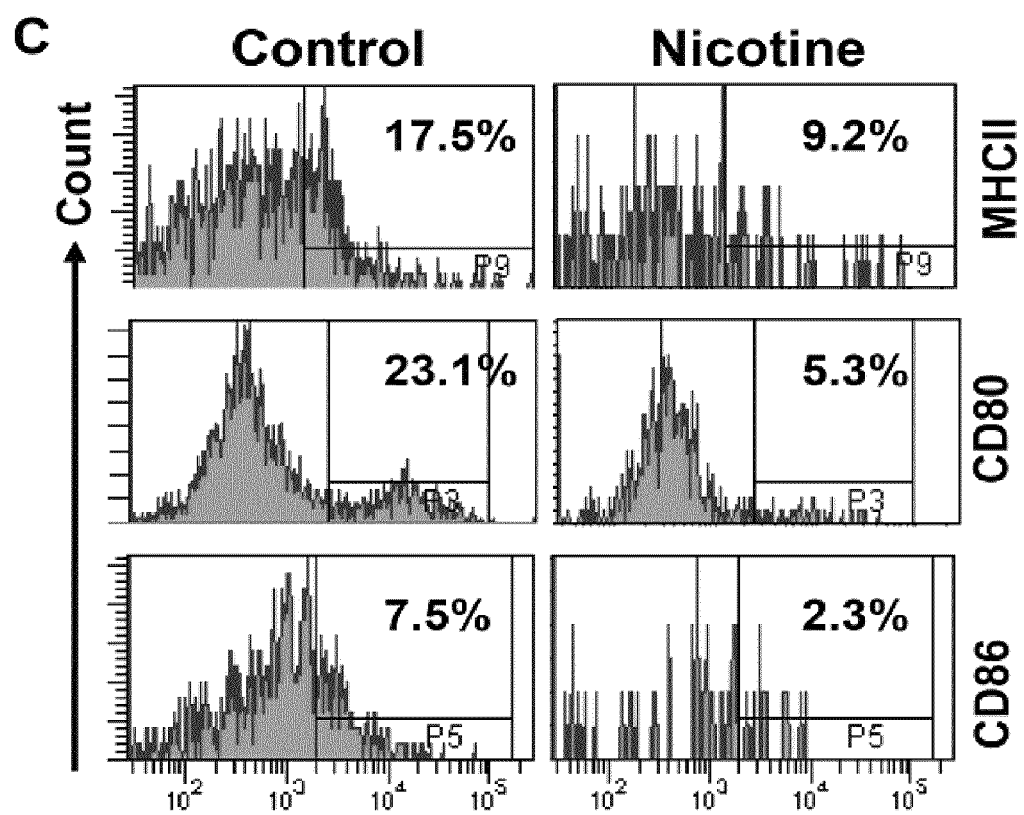
Figure 10:
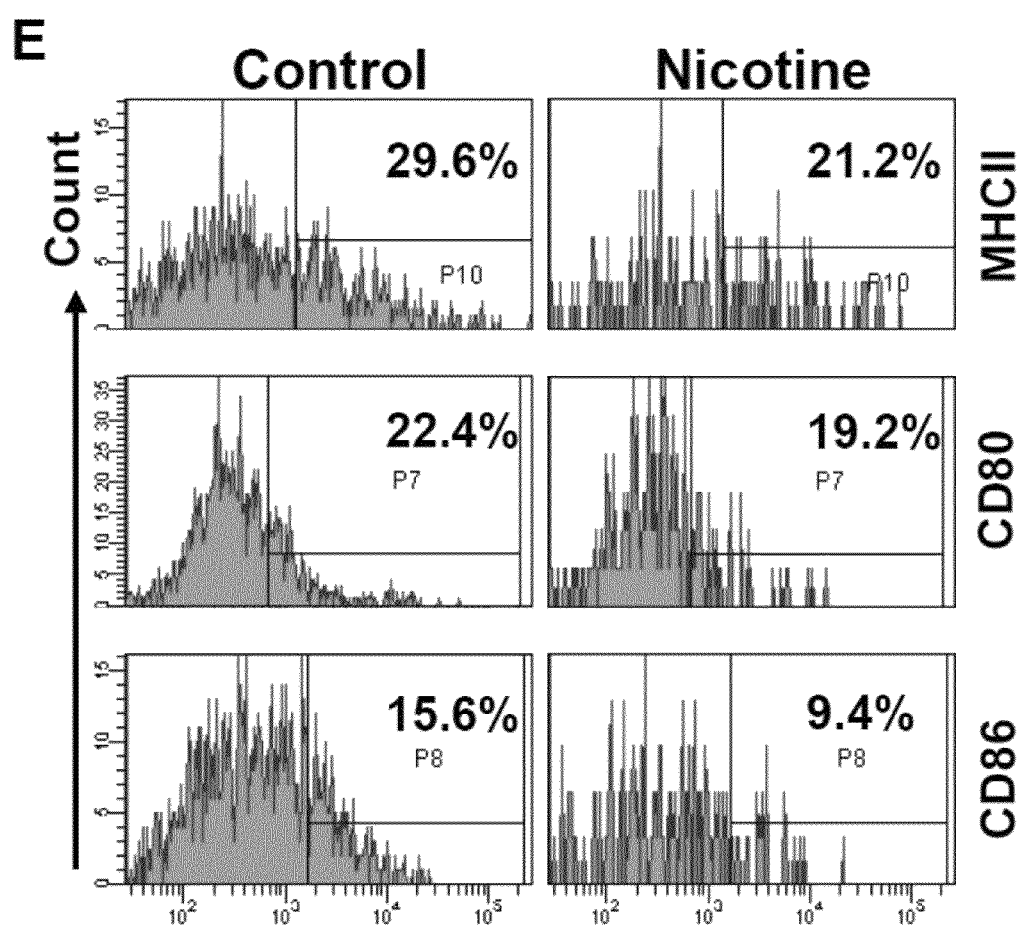

To determine whether nicotine is capable of altering the expression of EAE when myelin-reactive T cells become activated and early signs of disease begin to manifest, groups of mice were immunized with MOG and CFA. At day 7 p.i. when EAE signs began (flaccid tail, hind limb weakness, etc.), all immunized mice were randomly separated into two groups: one received PBS and the other nicotine. Compared with mice receiving PBS (maximal clinical score 3.3±0.25, mean clinical score 1.89 ±0.43), recipients of nicotine had significantly milder EAE (FIG. 1C, $p<0.05$ and $p<0.01$, respectively). Furthermore, nicotine improved their recovery from motor weakness over that of control mice ($p<0.01$, mean clinical score 0.69±0.43 at the termination of experiments). Therefore, the results clearly demonstrate that nicotine halted the progression of EAE when myelin-reactive cells were activated as signs of clinical EAE became visible.

EAE is a T-cell mediated disease in that it can be produced in recipients of encephalitogenic T cell transfers (McRae, B. L., et al., *J Neuroimmunol* 38:229-240). Thus, it was important to determine the capacity of myelin-reactive T cells from nicotine-treated mice to induce EAE. Accordingly, when the inventors performed adoptive transfers of T cells from nicotine-treated animals, as described herein, a milder form of EAE resulted than that from T cells of control mice (maximal clinical score 2.5±0.82 vs. 5.0±0.25 in nicotine-treated vs. control mice, respectively, p<0.001; mean clinical score 4.22±0.36 vs 1.0±0.15, p<0.001). Collectively, the results have shown that nicotine attenuated EAE when present before or after T cell activation, and that T cells from nicotine-treated mice significantly lowered the capacity to produce EAE in recipients of such transfers.

Example 14

Nicotine Ameliorates CNS Inflammation, Demyelination and Axonal Damage

Pronounced cellular infiltration, demyelination and axonal damage are pathological hallmarks of EAE and MS. To evaluate whether nicotine can alter these pathological changes, the inventors examined spinal cords from mice with ongoing EAE. In the white matter of these tissues from control mice, H&E and LFB staining revealed marked multi focal and lymphohistiocytic inflammation that was both perivascular and diffuse. Myelin loss was widespread, especially around inflamed areas. In sharp contrast, most sections from nicotine-treated mice had few infiltrating cells, and myelin sheets were largely preserved. Furthermore, axonal damage was clearly present in the sub-meningeal areas of PBS control mice, whereas axons from nicotine-treated mice were scarcely affected and then only in regions immediately surrounding foci of inflammation. Quantification showed that inflammation, demyelination and axonal degeneration were significantly greater in PBS-treated compared to nicotine-treated mice (p<0.01). Therefore, nicotine was responsible for protecting the CNS from inflammation, demyelination and axonal damage otherwise caused by EAE.

Example 15

Nicotine Alters the Peripheral Lymphocyte Subpopulation During EAE

Nicotine promotes the development of T and B cells during ontogeny (Middlebrook, A. J., et al., *J Immunol* 169:2915-2924; Skok, M., et al., *J Neuroimmunol* 171:86-98; Skok, M., et al., *Eur J Pharmacol* 517:246-251) and has pro- and anti-apoptotic activities for mature cells including lymphocytes (Zeidler, R., et al., *Apoptosis* 12:1927-1943). To address whether nicotine might alter the homeostasis of lymphocytes during an autoimmune response to MOG, the inventors quantified various lymphocyte subpopulations. For this and subsequent sections, cells from mice given nicotine at the day of MOG immunization (day 0) were used for immunological analysis. Results obtained from other time points were similar. Compared to control EAE mice, nicotine-treated mice had various degrees of reductions in the percentages and numbers of $CD3^+$, $CD4^+$ and $CD8^+$ T cells as well as $CD19^+$ $CD3^-$ B cells among splenocytes sampled on day 11 p.i. (p<0.05). With respect to NK ($CD3^-NK1.1^+$ cells) cells, NKT cells and $CD4^+CD25^+$ regulatory T cells, however, the values did not differ significantly between the nicotine-treated mice and PBS-treated mice at this time point. Interestingly, the expression of Foxp3 was clearly augmented in the nicotine-treated mice. Although the numbers and percentages of $CD11c^+$ and $CD11b^+$ cells were not dramatically altered by nicotine treatment, reductions in the expression of MHC class II, CD80 and CD86 were notable on these cells. Similar data were also obtained from assessments of lymph nodes and blood at several other time points during the course of EAE.

Example 16

Nicotine Inhibits Autoreactive T Cell Expansion

To address how nicotine affected expansion of $MOG_{33-55}$-specific T cell responses in PBS- vs. nicotine-treated EAE mice, mononuclear cells were isolated from their spleens, and the proliferation of T cells in response to myelin antigens was quantified using $^3H$ incorporation as well as CFSE assays. Splenocytes from PBS-treated controls and nicotine-treated groups mounted significant proliferative responses to MOG. However, the nicotine recipients developed far fewer T cells in response to the immunizing MOG antigen than did the PBS recipients (p<0.05 vs. PBS). Similarly, a reduced proliferation of $CD3^+$, $CD4^+$ and $CD8^+$ T cells in response to MOG was also recorded in nicotine-treated mice by using the CFSE assay. Next, annexin V and PI double staining were used to determine the effect of nicotine on T cell apoptosis and death. The results demonstrated that nicotine did not induce T cell apoptosis, at least at the current dose. Thus, the reduced numbers of several lymphocyte subpopulations recorded herein were the likely result of their decline in proliferation after nicotine exposure.

Example 17

Nicotine Alters Th Cell Cytokine Profile

To further characterize autoreactive T cells, the inventors investigated the effect of nicotine on cytokine production by Th cells. The inventors first detected cytokines in the supernatants of splenocytes cultured with $MOG_{35-55}$. There was a significant decrease of IFN-γ production in the nicotine-treated animals compared to controls. Further, the major contributors to this reduction appeared to be $CD8^+$ rather than $CD4^+$ cells. Similarly, the production of IL-2 decreased in the nicotine-treated animal. In contrast, production of IL-10 and TGF-β1 (p<0.05, p<0.01, respectively) was significantly augmented by nicotine treatment. Collectively, nicotine inhibited the myelin antigen-induced production of IFN-γ and IL-2 yet augmented the production of IL-10 and TGF-β.

Example 18

Nicotine Alters Autoantibody Isotypes

Autoantigen responses can reflect T cell help; for example, in mice, IFN-γ is believed to drive the IgG2b response, whereas the IgG1 response is driven by Th2 cells. The inventors therefore used an ELISA to measure MOG-specific antibodies in PBS- and nicotine-treated mice. Consistent with the Th cytokine profile, IgG2b production in nicotine-treated mice was profoundly impaired, whereas synthesis of IgG1 and IgA was markedly increased compared with that in control mice.

Example 19

Nicotine Alters Lymphocyte Subpopulations in the CNS During EAE

Histopathological studies revealed that less inflammatory infiltration occurs in CNS tissues of nicotine-treated animal than those of PBS-treated controls. To document nicotine's alteration of the cellular spectrum in the CNS during EAE, the inventors analyzed inflammatory cells that migrated into the CNS as well as residual microglia by isolating CNS mononuclear cells. As expected, T cells ($CD3^+$, $CD4^+$, $CD8^+$) and B cells ($CD3^-CD19^+$) were abundant in CNS sections from PBS-treated EAE mice, but their numbers were drastically reduced in the nicotine-treated mice.

Next, the inventors characterized APCs in the CNS during EAE. When quantifying the macrophage/microglia ($CD11b^+$ cells) and dendritic cell ($CD11c^+$ cells) populations in the CNS, the inventors found lower percentages and absolute numbers of $CD11b^+$ and $CD11c^+$ cells, particularly $CD11b^+$ cells, in the nicotine-treated mice. Further, the expression of MHC class II. CD80 and CD86 was reduced on the latter's CD11c and CD11b cells. It is important to note that, compared to results in the periphery, reductions in expression of MHC class II, CD80 and CD86 were much more dramatic on $CD11b^+$ cells of the CNS from the nicotine-treated animals. The unparalleled alteration in $CD11b^+$ cells from the CNS compared to the periphery implies that nicotine might be responsible for quite different effects in these two anatomical compartments.

Example 20

Conclusions

Expression of nicotinic acetylcholine receptors on non neuronal cells such as APCs underscores the idea that they have functions well beyond neurotransmission. Previous studies indicate that nicotine exerts anti-inflammatory and immune modulatory effects in vivo (Sopori., M., *Nat Rev Immunol* 2:372-377). However, its role in CNS inflammation and autoimmune responses was not known. Using the EAE model, the inventors have now demonstrated that nicotine can dramatically attenuate the infiltration of inflammatory cells into the CNS as well as the related destruction of myelin and axons. The results thus reveal new aspects of the way in which nicotine functions as a potent immune modulator within the CNS and highlight the importance of understanding interactions between the nervous system and immune system when seeking means to ameliorate CNS inflammatory disorders.

Example 21

Nicotine Dosing in Mice and Humans

Nicotine bitartrate was delivered using osmotic minipumps implanted subcutaneously in mice (100 mg/ml; molecular mass of 498 daltons or grams/mole as the dihydrate; 12 µl/d; equates to 0.39 mg of nicotine free base per mouse per day). For a ~30 gm mouse, this equates to ~43 mg of nicotine free base/kg/d or ~0.54 mg of nicotine free base/kg/hr. Published literature indicates that plasma nicotine levels in mice are ~200 ng/ml (~1.2 µM) after infusion of 4 mg/kg/hr of drug and ~45 ng/ml (~280 nM) after infusion at ~0.5 mg/kg/hr. For comparison, human heavy smokers have plasma nicotine levels of 15-38 ng/ml (~90-230 nM). Thus, nicotine levels in plasma of mice used in the studies are comparable to those in the plasma of human smokers.

Example 22

Table 1—Nicotinic Analogs and/or Deriviatives

Table 1 lists various examples of nicotinic receptor agents, as well as possible sources in the literature that describe the corresponding substance in greater detail. Nicotinic receptor agents include nicotine, pharmaceutical equivalents, analogs, derivatives, and salts thereof, that may be used in conjunction with various embodiments described herein. In one embodiment, a therapeutically effective dosage of a substance described in Table 1 below may be administered to a subject to treat a degenerative disease of the central nervous system (CNS). Additionally, various examples of nictonic receptor agents are also described in references Horenstein, et al., Mol Pharmacol 74:1496-51 1, 2008, and Arneric, et al., Biochemical Pharmacology 74 (2007) 1092-1101, incorporated by reference herein.

TABLE 1

| Substance | Source |
|---|---|
| cytisine | *Acta Polon Pharm* 29(5): 490; 1972 |
| | *Biokhimiia* 43(7): 1150; 1978 |
| nicotine polacrilex | *Compr Ther* 1987; 13(3): 32 |
| nornicotine | *Environ N-Nitroso Cpds Anal Forum W1* 121k No. 14: 227; 1976 |
| | *J Org Chem* 41(21): 3438; 1976 |
| nicotine 1-N-oxide | *Appl Environ Microbiol* 1979; 38(5): 836 |
| metanicotine | *J Pharmacol Exp Ther* 196(3): 685; 1976 |
| nicotine imine | *Adv Exp Med Biol* 1982; 136B: 1121 |
| nicotine N-glucuronide | *J Chromatogr* 1993 Nov 17; 621(1): 49-53 |
| N-methylnicotinium | *J Chromatogr* 1985; 347(3): 405 |
| N-n-decylnicotinium | *Br J Pharmacol* 1999 Nov; 128(6): 1291-9 |
| 5'-cyanonicotine | *J Biol Chem* 248(8): 2796; 1973 |
| 3,4-dihydrometanicotine | *Klin Wochenschr* 1984; 62 suppl 2: 92 |
| N'-methylnicotinium | *Pharmacol Biochem Behav* 1991; 38(4): 843 |
| N-octanoylnornicotine | *Endocr Res* 1991; 17(3-4): 409-19 |
| 2,3,3a,4,5,9b-hexahydro-1-methyl-1H-pyrrolo(3,2-h)isoquinoline | *J Med Chem* 1993 Oct 29; 36(22): 3381-5 |
| 5-isothiocyanonicotine | *Biochem Pharmacol* 1994 Jun 1; 47(11): 1965-7 |
| 5-iodonicotine | *Biol Pharm Bull* 1995 Nov; 18(11): 1463-6 |
| 5'-hydroxycotinine-N-oxide | *Xenobiotica* 1999 Aug; 29(8): 793-801 |
| homoazanicotine | *J Med Chem* 2002 Oct 10; 45(21): 4724-31 |

TABLE 1-continued

| Substance | Source |
|---|---|
| nicotine monomethiodide | *Naunyn Schmiedebergs Arch Pharmacol* 22(282): R69; 1974 |
| N-4-azido-2-nitrophenylnornicotine | *Ann NY Acad Sci* 1980; 346: 419 |
| N-methylnornicotinium | *Drug Metab Dispos* 1985; 13(3): 348 |
| nicotinium molybdophosphate resin | *Bull Environ Contam Toxicol* 1986; 36(6): 924 |
| N-methyl-N'-oxonicotinium | *Drug Metab Dispos* 1986; 14(5): 574 |
| N'-propylnornicotine | *J Chromatogr* 1990; 525(2): 349 |
| pseudooxynicotine | *Ann N Y Acad Sci* 1993 May 28; 686: 213-28 |
| 4'-methylnicotine | *J Med Chem* 1994 Oct 14; 37(21): 3542-53 |
| 5-fluoronicotine | *Neurochem Res* 1995 Sep; 20(9): 1089-94 |
| K(s-nic)5(Ga2(N,N'-bis-(2,3-dihydroxybenzoyl)-1,4-phenylenediamine)3) | *Inorg Chem* 2001 May 7; 40(10): 2216-7 |
| 5-methoxynicotine | *Eur J Pharmacol* 2002 Jan 25; 435(2-3): 171-80 |
| 1-benzyl-4-phenylnicotinamidinium | *J Am Chem Soc* 2002 Aug 7; 124(31): 9181-8 |
| 6-n-propylnicotine | *Bioorg Med Chem Lett* 2002 Oct 21; 12(20): 3005-7 |
| SIB1663 | *Brain Res* 2004 Apr 2; 1003(1-2): 42-53 |
| 6-hydroxynicotine | *Nucleic Acids Res* 2005; 33(12) (dup#1): e107 |
| N-methyl-nicotine | *Biol Reprod.* 2005 Mar; 72(3): 628-32 |
| 6-(2-phenylethyl)nicotine | *Bioorg Med Chem Lett* 2005 Jul 1; 15(13): 3237-40 |
| N'-formylnornicotine | *Phytochemistry* 2005 Oct; 66(20): 2432-40 |
| N-n-octylnicotinium | *AAPS J* 2005; 7(1): E201-17 |
| N-(n-oct-3-enyl)nicotinium | *AAPS J* 2005; 7(1): E201-17 |
| N-(n-dec-9-enyl)nicotinium | *AAPS J* 2005; 7(1): E201-17 |
| 5'-acetoxy-N'-nitrosonornicotine | *Chem Res Toxicol* 2006 Mar; 19(3): 426-35 |
| 4-hydroxynicotine | *Org Lett.* 2005 Oct 27; 7(22): 5059-62 |
| 4-(dimethylphenylsilyl)nicotine | *Org Lett.* 2005 Oct 27; 7(22): 5059-62 |
| N'-carbomethoxynornicotine | *J Nat Can Inst* 54(5): 1238; 1975 |
| N-methylnicoton | *Arch Pharm (Weinheim)* 309(3): 197; 1976 |

While the description above refers to particular embodiments of the present invention, it should be readily apparent to people of ordinary skill in the art that a number of modifications may he made without departing from the spirit thereof. The presently disclosed embodiments are, therefore, to be considered in all respects as illustrative and not restrictive.

Various embodiments of the invention are described above in the Detailed Description. While these descriptions directly describe the above embodiments, it is understood that those skilled in the art may conceive modifications and/or variations to the specific embodiments shown and described herein. Any such modifications or variations that fall within the purview of this description are intended to be included therein as well. Unless specifically noted, it is the intention of the inventor that the words and phrases in the specification and claims be given the ordinary and accustomed meanings to those of ordinary skill in the applicable art(s).

The foregoing description of various embodiments of the invention known to the applicant at this time of filing the application has been presented and is intended for the purposes of illustration and description. The present description is not intended to be exhaustive nor limit the invention to the precise form disclosed and many modifications and variations are possible in the light of the above teachings. The embodiments described serve to explain the principles of the invention and its practical application and to enable others skilled in the art to utilize the invention in various embodiments and with various modifications as are suited to the particular use contemplated. Therefore, it is intended that the invention not be limited to the particular embodiments disclosed for carrying out the invention.

While particular embodiments of the present invention have been shown and described, it will be obvious to those skilled in the art that, based upon the teachings herein, changes and modifications may be made without departing from this invention and its broader aspects and, therefore, the appended claims are to encompass within their scope all such changes and modifications as are within the true spirit and scope of this invention. Furthermore, it is to be understood that the invention is solely defined by the appended claims. It will be understood by those within the art that, in general., terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to inventions containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations).

Accordingly, the invention is not limited except as by the appended claims.

The invention claimed is:

1. A method of treating a disease or condition in a subject, wherein the subject is a mouse, comprising:
   providing a composition comprising a nicotinic receptor agent; and
   administering a therapeutically effective dosage of the composition to the subject, wherein the therapeutically effective dosage of the nicotinic receptor agent ranges from 1 mg nicotine free base/kg to 60 mg nicotine free base/kg or wherein the therapeutically effective dosage of the nicotinic receptor agent is about 13 mg nicotine free base/kg/day administered over a period of 7 days.

2. The method of claim 1, wherein the therapeutically effective dosage of the nicotinic receptor agent is about 13 mg nicotine free base/kg/day administered over a period of 7 days.

3. A method of treating a disease or condition in a subject, wherein the subject is a human, comprising:
   providing a composition comprising and
   administering a therapeutically effective dosage of the composition to the subject, wherein the therapeutically effective dosage of the nicotinic receptor agent ranges from nicotine plasma levels of 1 ng/mL to 100 ng/mL or wherein the therapeutically effective dosage of the nicotinic receptor agent is a nicotine plasma level of about 30 ng/mL.

4. The method of claim 3, wherein the therapeutically effective dosage of the nicotinic receptor agent is a nicotine plasma level of about 30 ng/mL.

5. A method of treating a disease or condition in a subject, comprising:
   providing a composition comprising a nicotinic receptor agent; and
   administering a therapeutically effective dosage of the composition to the subject, wherein the disease or condition is multiple sclerosis (MS), acute disseminated encephalomyelitis, or experimental autoimmune encephalomyelitis (EAE).

6. The method of claim 5, wherein the disease or condition is acute disseminated encephalomyelitis.

7. The method of claim 5, wherein the disease or condition is experimental autoimmune encephalomyelitis (EAE).

8. The method of claim 5, wherein the nicotinic receptor agent is administered to the subject continuously by an implanted pump.

9. A method of treating a disease or condition in a subject, comprising:
   providing a composition comprising a nicotinic receptor agent; and
   administering a therapeutically effective dosage of the composition to the subject, wherein the nicotinic receptor agent comprises nicotine bitartrate.

10. The method of claim 1, wherein the therapeutically effective dosage of the nicotinic receptor agent ranges from 1 mg nicotine free base/kg to 60 mg nicotine free base/kg.

11. The method of claim 3, wherein the therapeutically effective dosage of the nicotinic receptor agent ranges from nicotine plasma levels of 1 ng/mL to 100 ng/mL.

12. The method of claim 5, wherein the disease or condition is multiple sclerosis (MS).

* * * * *